US00RE40594E

(19) United States
(12) Reissued Patent
Margolskee et al.

(10) Patent Number: US RE40,594 E
(45) Date of Reissued Patent: Dec. 2, 2008

(54) INHIBITORS OF THE BITTER TASTE RESPONSE

(75) Inventors: Robert F. Margolskee, Upper Montclair, NJ (US); Ding Ming, Whippany, NJ (US)

(73) Assignee: Mount Sinai School of Medicine of New York University, New York, NY (US)

(21) Appl. No.: 11/391,670

(22) Filed: Mar. 28, 2006

Related U.S. Patent Documents

Reissue of:
(64) Patent No.: 6,540,978
Issued: Apr. 1, 2003
Appl. No.: 09/470,467
Filed: Dec. 22, 1999

U.S. Applications:
( 60) Provisional application No. 60/113,562, filed on Dec. 23, 1998.

(51) Int. Cl.
*A61K 49/00* (2006.01)

(52) U.S. Cl. ..... 424/9.2; 424/1.11; 424/9.1; 424/1.65

(58) Field of Classification Search ..... 424/1.11, 424/1.65, 9.1, 9.2; 435/7.1
See application file for complete search history.

(56) References Cited

U.S. PATENT DOCUMENTS

| | | | |
|---|---|---|---|
| 3,505,082 | A | 4/1970 | Miller |
| 3,647,482 | A | 3/1972 | Yueh |
| 3,784,390 | A | 1/1974 | Hijiya et al. |
| 3,860,732 | A | 1/1975 | Eisenstadt |
| 3,872,227 | A | 3/1975 | Hoff et al. |
| 4,243,691 | A | 1/1981 | Mohlenkamp, Jr et al. |
| 4,297,375 | A | 10/1981 | Shackelford |
| 4,376,132 | A | 3/1983 | Eguchi et al. |
| T104,004 | I4 | 3/1984 | von Rymon Lipinski |
| 4,514,431 | A | 4/1985 | Buckholz, Jr. et al. |
| 4,544,559 | A | 10/1985 | Gil et al. |
| 4,560,574 | A | 12/1985 | Meyer |
| 4,562,020 | A | 12/1985 | Hijiya et al. |
| 4,563,359 | A | 1/1986 | Shimizu et al. |
| 4,567,047 | A | 1/1986 | SCM Corporation |

(Continued)

FOREIGN PATENT DOCUMENTS

| | | | |
|---|---|---|---|
| CH | 497 136 | | 11/1970 |
| DE | 33 31 517 | A1 | 3/1984 |
| EP | 0 059 363 | B1 | 12/1984 |
| EP | 0 122 400 | B1 | 7/1987 |
| EP | 0 125 021 | B1 | 7/1987 |
| EP | 0 291 980 | B1 | 1/1992 |
| EP | 0 416 667 | B1 | 9/1993 |
| JP | 48-17044 | B4 | 3/1973 |
| JP | 48-10227 | B4 | 4/1973 |
| JP | 59-55165 | A | 3/1984 |
| JP | 59-210866 | A | 11/1984 |
| JP | 61-271969 | A2 | 12/1986 |
| JP | H1-285157 | A | 11/1989 |
| JP | 4-40881 | A | 2/1992 |
| JP | H5-236885 | A | 9/1993 |
| JP | H10-108655 | A | 4/1998 |
| JP | 11-169131 | A | 6/1999 |
| JP | 2003/00206 | A | 10/2000 |
| RU | 2003265 | C1 | 11/1993 |
| WO | WO 91/09955 | A1 | 7/1991 |
| WO | WO 92/20808 | A1 | 11/1992 |
| WO | WO 94/12650 | A2 | 6/1994 |
| WO | WO 97/04666 | A1 | 2/1997 |
| WO | WO 98/20862 | A2 | 5/1998 |
| WO | WO 98/26763 | A1 | 6/1998 |
| WO | WO 98/26780 | A2 | 6/1998 |
| WO | WO 99/17753 | A1 | 4/1999 |
| WO | WO 00/38536 | A2 | 7/2000 |
| WO | WO 02/096464 | A1 | 12/2002 |
| WO | WO 03/075661 | A1 | 9/2003 |

OTHER PUBLICATIONS

Anderson et al., "Potassium and Health," Colorado State University Cooperative Extension—Nutrition Resources No. 9.355, at http://www.ext.colostate/edu/pubs/foodnut/09355.html (Apr. 8, 2005).

Answers.Com™, "Food Additive" at http://www.answers.com/topic/food–additive (accessed Jun. 6, 2005).

Chiou & Lai, "Comparison of Taste Components in Cooked Meats of Small Abalone Fed Different Diets," *Fisheries Science* 68:388–394 (2002).

Chiou et al., "Seasonal Variations of Chemical Constituents in the Muscle and Viscera of Small Abalone Fed Different Diets," *Fisheries Science* 67:146–156 (2001).

Chiou, "Utilization of Cooking Waste of Canned Tuna as Flavorings. 3. Nitrogenous Constituents of the Extract and their Taste Preference," *Food Science* pp.208–217 (1991).

Danilova et al., "Responses of Single Taste Fibers and Whole Chorda Tympani and Glossopharyngeal Nerve in the Domestic Pig, *Sus scrofa*," *Chem. Senses* 24:301–316 (1999).

EDLONG®, "Cheese Flavors," Edlong Dairy, at http://www.edlong.com/flavors/cheese.asp (accessed Jun. 17, 2005).

Engel et al., "Determination of Taste–active Compounds of a Bitter Camembert Cheese by Omission Tests," *J. Dairy Res.* 68:675–688 (2001).

(Continued)

*Primary Examiner*—Dameron L. Jones
(74) *Attorney, Agent, or Firm*—Nixon Peabody LLP

(57) ABSTRACT

The present invention relates to methods for identifying inhibitors of the bitter taste response, and by methods of using such inhibitors to either block the perception of bitterness and/or promote the perception of a sweet taste. The inhibitors of the invention may be used as flavor enhancers in foods and pharmaceuticals. The methods of the invention may further be used to characterize the gustatory perception of novel tastants.

103 Claims, 7 Drawing Sheets

U.S. PATENT DOCUMENTS

Figure 1A:
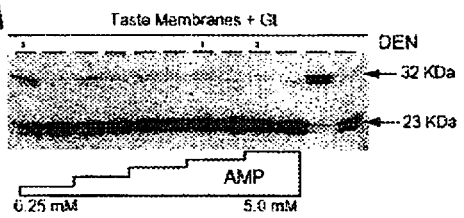

| | | | |
|---|---|---|---|
| 4,600,708 | A | 7/1986 | Reuter et al. |
| 4,623,394 | A | 11/1986 | Nakamura et al. |
| 4,820,506 | A | 4/1989 | Kleinberg et al. |
| 4,826,824 | A | 5/1989 | Schiffman |
| 4,851,394 | A | 7/1989 | Kubodera |
| 4,921,939 | A | 5/1990 | Nofre et al. |
| 4,963,387 | A | 10/1990 | Nakagawa et al. |
| 4,994,442 | A | 2/1991 | Gil et al. |
| 5,145,707 | A | 9/1992 | Lee |
| 5,173,323 | A | 12/1992 | Omari |
| 5,232,735 | A | 8/1993 | Kurtz et al. |
| 5,372,834 | A | 12/1994 | Buckholz, Jr. et al. |
| 5,411,945 | A | 5/1995 | Ozaki et al. |
| 5,518,902 | A | 5/1996 | Ozaki et al. |
| 5,589,357 | A | 12/1996 | Martinez et al. |
| 5,631,038 | A | 5/1997 | Kurtz et al. |
| 5,631,231 | A | 5/1997 | Kurtz et al. |
| 5,631,232 | A | 5/1997 | Kurtz et al. |
| 5,631,240 | A | 5/1997 | Kurtz et al. |
| 5,631,252 | A | 5/1997 | Kurtz et al. |
| 5,631,272 | A | 5/1997 | Kurtz et al. |
| 5,631,292 | A | 5/1997 | Kurtz et al. |
| 5,631,294 | A | 5/1997 | Kurtz et al. |
| 5,631,295 | A | 5/1997 | Kurtz et al. |
| 5,631,299 | A | 5/1997 | Kurtz et al. |
| 5,637,618 | A | 6/1997 | Kurtz et al. |
| 5,639,788 | A | 6/1997 | Kurtz et al. |
| 5,641,795 | A | 6/1997 | Kurtz et al. |
| 5,641,799 | A | 6/1997 | Kurtz et al. |
| 5,641,811 | A | 6/1997 | Kurtz et al. |
| 5,641,812 | A | 6/1997 | Kurtz et al. |
| 5,643,894 | A | 7/1997 | Kurtz et al. |
| 5,643,941 | A | 7/1997 | Kurtz et al. |
| 5,643,945 | A | 7/1997 | Kurtz et al. |
| 5,643,955 | A | 7/1997 | Kurtz et al. |
| 5,643,956 | A | 7/1997 | Kurtz et al. |
| 5,646,122 | A | 7/1997 | Kurtz et al. |
| 5,650,403 | A | 7/1997 | Kurtz et al. |
| 5,654,311 | A | 8/1997 | Kurtz et al. |
| 5,665,755 | A | 9/1997 | Kurtz et al. |
| 5,693,756 | A | 12/1997 | Li et al. |
| 5,700,792 | A | 12/1997 | Kurtz et al. |
| 5,703,053 | A | 12/1997 | Kurtz et al. |
| 5,789,250 | A | 8/1998 | Ikezaki |
| 5,817,759 | A | 10/1998 | Margolskee |
| 5,853,792 | A | 12/1998 | Zolotov et al. |
| 5,866,608 | A | 2/1999 | Kurtz et al. |
| 5,897,908 | A | 4/1999 | Berglund et al. |
| 6,008,250 | A | 12/1999 | Kurtz et al. |
| 6,015,792 | A | 1/2000 | Kurtz et al. |
| 6,368,651 | B1 | 4/2002 | Gerlat et al. |
| 6,541,050 | B1 | 4/2003 | Bonorden et al. |
| 6,783,788 | B2 | 8/2004 | Kuroda et al. |
| 6,942,874 | B2 | 9/2005 | McGregor et al. |
| 2001/0022964 | A1 | 9/2001 | Leung et al. |
| 2003/0035875 | A1 | 2/2003 | Dulebohn et al. |
| 2003/0157568 | A1 | 8/2003 | Zuker et al. |
| 2003/0166103 | A1 | 9/2003 | Huang et al. |
| 2003/0194423 | A1 | 10/2003 | Torney et al. |

OTHER PUBLICATIONS

Fuke, "Taste–active Components of Seafoods with Special Reference to Umami Substances," in Seafoods: Chemistry, Processing Technology and Quality 115–139 (Fereidoon Shahidi & J. Richard Botta eds., (1994).

Gravina et al., "Biomimetic In Vitro Assay for the Characterization of Bitter Tastants and Identification of Bitter Taste Blockers," in 867 ACS Symposium Series 91–101 (Thomas Hofmann et al. eds., 2004).

Harder et al., "Assessing Gustatory Detection Capabilities Using Preference Procedures," *Chem. Senses* 14(4):547–564 (1989).

Hayashi et al., "Sensory Study of Flavour Compounds in Extracts of Salted Salmon Eggs (Ikura)," *J. Sci. Food Agric.* 50(3):343–356 (1990).

Heath & Reineccius, "Flavor Potentiators," in Flavor Chemistry and Technology 318–331 (1986).

Hwang et al., "Seasonal Variations of Free Amino Acids and Nucleotide–related Compounds in the Muscle of Cultured Taiwanese Puffer *Takifugu rubripes," Fisheries Science* 66:1123–1129 (2000).

Jingami et al., "Structure of the Metabotripic Glutamate Receptor," *Curr. Opin. Neurobiol.* 13:271–278 (2003).

Koga et al., "Free Amino Acids, Carnosine and 5'–Inosinic Acid Contents in the Beef Loin and Beef Round," *Mem. Fac. Agr. Kagoshima Univ.* 23:121–129 (1987).

Komata, "Umami Taste of Seafoods," *Food Reviews International* 6(4):457–487 (1990).

Kuramitsu et al., "Tastes Produced by Peptides Containing Ionic Groups and by Related Compounds," *Biosci. Biotech. Biochem.* 60(10):1637–1642 (1996).

Kuramitsu, "Quality Assessment of a Low–salt Soy Sauce Made of a Salty Peptide or Its Related Compounds," *Adv. Exp. Med. Biol.* 542:227–238 (2004).

Lee et al., "Seasonal Variations of Taste Components in Warty Sea Squirt (*Styela clava*)," *J. Korean Soc. Food Nutr.* 24(2):274–279 (1995).

Maehashi et al., "Isolation of Peptides from an Enzymatic Hydrolysate of Food Proteins and Characterization of Their Taste Properties," *Biosci. Biotechnol. Biochem.* 63(3):555–559 (1999).

McCormick®, "Spices & Seasonings," at http://www.mccormick.com/content.cfm?id=7056 (accessed Jun. 2, 2005).

McGregor & Gravina, "Studies of the Blocking of Bitter Taste," *23rd Meeting of Association of Chemoreceptor Science* (2001) (abstract only).

McGregor, "Taste Modification in the Biotech Era," *Foodtechnology* 58(5):24–25, 28–30 (2004).

Michikawa & Konosu, "Sensory Identification of Effective Components for Masking Bitterness of Arginine in Synthetic Extract of Scallop," *Olfaction and Taste XI 278* (Kenzo Kurihara et al. eds., Jul. 12–16, 1993).

Mojet et al., "Effect of Concentration on Taste–taste Interactions in Foods for Elderly and Young Subjects," *Chem. Senses* 29:671–681 (2004).

Nakata et al., "Role of Basic and Acidic Fragments in Delicious Peptides (Lys–Gly–Asp–Glu–Glu–Ser–Leu–Ala) and the Taste Behavior of Sodium and Potassium Salts in Acidic Oligopeptides," *Biosci. Biotech. Biochem.* 59(4):689–693 (1995).

Noguchi et al., "On the Bitter–masking Activity of a Glutamic Acid–rich Oligopeptide Fraction," *J. Food Sci.* 40(2):367–369 (1975).

NUTRITIONDATA.COM, "Food Additives," at http://www.nutritiondata.com/food–additives.html (Jun. 6, 2005).

Ohyama et al., "Synthesis of Bitter Peptides Composed of Aspartic Acid and Glutamic Acid," *Agric. Biol. Chem.* 52(3):871–872 (1988).

Schiffman et al., "Effect of the Nucleoside Analogs Zidovudine, Didanosine, Stavudine, and Lamivudine on the Sense of Taste," *Nutrition* 15(11/12):854–859 (1999).

Schiffman et al., "Modulators of the Adenylate Cyclase System Can Alter Electrophysiological Taste Responses in Gerbil," *Pharmacol. Biochem. and Behav.* 48(4):983–990 (1994).

Seki et al., "Further Study on the Salty Peptide Ornithyl–β–alanine. Some Effects of pH and Additive Ions on the Saltiness," *J. Agric. Food Chem.* 38:25–29 (1990).

Shiau et al., "Extractive, Nitrogenous Components of Oysters (*Crassostrea virginica*) and Their Released Liquors," *J. Fish. Soc. Taiwan* 21(3):381–291 (1994).

Shirai et al., "Taste Components of Japanese Spiny and Shovel–nosed Lobsters," *Fisheries Science* 62(2):283–287 (1996).

Tada et al., "L–Ornithyltaurine, a New Salty Peptide," *J. Agric. Food Chem.* 32:992–996 (1984).

Tamura et al., "An Enhancing Effect on the Saltiness of Sodium Chloride of Added Amino Acids and Their Esters," *Agric. Biol. Chem.* 53(6):1625–1633 (1989).

Tamura et al., "Mechanism for the Bitter Tasting Potency of Peptides Using O–Aminoacyl Sugars as Model Compounds," *Agric. Biol. Chem.* 54(6):1401–1409 (1990).

Tamura et al., "Practical Debittering Using Model Peptides and Related Compounds," *Agric. Biol. Chem.* 54(1):41–51 (1990).

Tamura et al., "Structural Correlation between Some Amides and a Taste Receptor Model," *J. Agric. Food Chem.* 37:737–740 (1989).

Tamura et al., "The Relationship between Taste and Primary Structure of 'Delicious Peptide' (Lys–Gly–Asp–Glu–Glu–Ser–Leu–Ala) from Beef Soup," *Agric. Biol. Chem.* 53(2):319–325 (1989).

U.S. Dairy Export Council, "Industry Overview," at http://www.usdec.org/Products/CheeseSpecs/content.cfm?Item-number=420 (accessed Jun.l 17, 2005).

Whole Foods Market, "Inactive Ingredients (Excipients)," at http://www.wholefoodmarket.com/healthinfo/excipients.html (accessed Jun. 6, 2005).

Xu et al., "Different Functional Roles of TIR Submits in the Heteromeric Taste Receptors," *PNAS* 101(39):14258–14263 (2004).

Yamaguchi et al., "The Synergistic Taste Effect of Monosodium Glutamate and Disodium 5'–Inosinate," *J. Food Sci.* 32:473–478 (1967).

Yamaguchi, "Basic Properties of Umami and Effects on Humans," *Physiol. Behav.* 49:833–841 (1991).

Yang & Lee, "Taste Compounds of Fresh–water Fishes 8. Taste Compounds of Crucian Carp Meat," *Bull. Korean Fish. Soc.* 17(3):170–176 (1984).

#20729, "Sodium–free Salt Substitute," *Res. Disclosure Index* 262–263 (1981).

Merck & Co. Inc., The Merck Index 456, 779, 780, 854, 1553 (Susan Budavari et al. eds., 12$^{th}$ ed. 1996).

REVIEW, "Salt–free Salt," *Nutrition Reviews* 43(11):337–338 (1985).

Baglien, "Necessity for Maintaining Tier 1 Sodium Level Requirement for Healthy Claims on Meat and Poultry Products to Achieve Food Safety, Consumer Acceptability and Dietary Guidelines," in Letter from Brent A. Baglien, Vice President Government Affairs, ConAgra Foods, Inc., to Dockets Management Branch, Food and Drug Administration (Nov. 30, 2004).

Letter from Mark L. McGowan, Chief Counsel—Foods Division, Quaker Foods & Beverages, and Dr. Steven Ink, Director—Nutrition Services, Quaker Foods & Beverages, to Dockets Management Branch, Food and Drug Administration (Jul. 10, 2003).

McLaughlin et al., "Gustducin and Transducin: A Tale of Two G Proteins," *Ciba Foundation Symposium* 179:186–200 (1993).

Naim et al., "Some Taste Substances are Direct Activators of G–proteins," *Biochem. J.* 297:451–454 (1994).

Ruiz–Avila et al., "Coupling of Bitter Receptor to Phosphodiesterase Through Transducin in Taste Receptor Cells," *Nature* 376:80–85 (1995).

Spielman, "Gustducin and Its Role in Taste," *J. Dent. Res.* 77(4);539–544 (1998).

Boughter, Jr. et al., "Differential Expression of α–Gustducin in Taste Bud Populations of the Rat and Hamster," *J. Neurosci.* 17(8):2852–2858 (1997).

Huang et al., "Gγ13 Colocalizes with Gustducin in Taste Receptor Cells and Mediates $IP_3$ Responses to Bitter Denatonium," *Nature Neurosci.* 2(12):1055–1062 (1999).

Hoon et al., "Putative Mammalian Taste Receptors: A Class of Taste–specific GPCRs with Distinct Topographic Selectivity," *Cell* 96:541–551 (1999).

Rosenzweig et al., "Possible Novel Mechanism for Bitter Taste Mediated Through cGMP," *Am. Physiol. Soc.* 81:1661–1665 (1999).

Ming et al., "Blocking Taste Receptor Activation of Gustducin Inhibits Gustatory Responses to Bitter Compounds," *Proc. Natl. Acad. Sci. USA* 96:9903–9908 (1999).

Rössler et al., "Identification of a Phospholipase C β Subtype in Rat Taste Cells," *Eur. J. Cell. Biol.* 77:253–261 (1998).

Spielman et al., "Rapid Kinetics of Second Messenger Production in Bitter Taste," *Am. Physiol. Soc.* 270:C926–C931 (1996).

Lindemann, "Taste Reception," *Physiol. Rev.* 76(3):719–766 (1996).

Spielman et al., "Generation of Inositol Phosphates in Bitter Taste Tranduction," *Physiology & Behavior* 56(6):1149–1155 (1994).

Akabas et al., "A Bitter Substance Induces a Rise in Intracellular Calcium in a Subpopulation of Rat Taste Cells," *Science* 242:1047–1050 (1988).

Ming et al., "Characterization and Solubilization of Bitter–responsive Receptors that Couple to Gustducin," *Proc. Natl. Acad. Sci. USA* 95:8933–8938 (1998).

Wong et al., "Transduction of Bitter and Sweet Taste by Gustducin," *Nature* 381:796–800 (1996).

Kinnamon & Margolskee, "Mechanisms of Taste Transduction," *Curr. Opin. Neurobiol:* 6:506–513 (1996).

McLaughlin et al., "Molecular Cloning of G Proteins and Phosphodiesterases from Rat Taste Cells," *Physiology & Behavior* 56:1157–1164 (1994).

McLaughlin et al., "Gustducin is a Taste–cell–specific G Protein Closely Related to the Transducins," *Nature* 357:563–569 (1992).

Chaudhari & Roper, "Molecular and Physiological Evidence for Glutamate (Umami) Taste Transduction via a G Protein–coupled Receptor," *Ann. NY Acad. Sci.* 855:398–406 (1998).

Chaudhari et al., "The Taste of Monosodium Glutamate: Membrane Receptors in Taste Buds," *J. Neurosci.* 16(12):3817–3826 (1996).

Wong et al., "Biochemical and Transgenic Analysis of Gustducin's Role in Bitter and Sweet Transduction," *Cold Spring Harbor–Symp. Quant. Biol.* 61(2):173–184 (1996).

Hamm et al., "Site of G Protein Binding to Rhodopsin Mapped with Synthetic Peptides from the α Subunit," *Science* 241(4867):832–835 (1988).

Medynski et al., "Amino Acid Sequence of the α Subunit of Transducin Deduced from the cDNA Sequence," *Proc. Natl. Acad. Sci. USA* 82(13):4311–4315 (1985).

Tanabe et al., "Primary Structure of the α–Subunit of Transducin and Its Relationship to *ras* Proteins," *Nature* (*London*) 315(6016):242–245 (1985).

Ninomiya et al., "Lack of Gurmarin Sensitivity of Sweet Taste Receptors Innervated by the Glossopharyngeal Nerve in C57BL Mice," *Am. J. Physiol.* (*London*) 272(3 Pt 2):R1002–R1006 (1997).

Ninomiya et al., "Gustatory Neural Responses in Three Different Strains of Mice," *Brain Res.* 302(2):305–314 (1984).

McLaughlin et al (1993), The molecular basis of smell and taste transductin. Ciba Foundation Symposium, vol. 179, pp. 186–200.*

Amer & Kreighbaum, "Cyclic Nucleotide Phosphodiesterases: Properties, Acitvators, Inhibitors, Structure–Activity Relationships, and Possible Role in Drug Development," *J. Pharm. Sci.* 64(1):1–37 (1975).

Asano et al., "Reconstitution of Cathcolamine–stimulated Binding of Guanosine 5'–O–(3–Thiotriphosphate) to the Stimulatory GTP–binding Protein of Adenylate Cyclase," *Biochem*. 23:5460–7 (1984).

Avenet & Lindemann, "Perspectives of Taste Reception," *J. Membr. Biol*. 112(1):1–8 (1989).

Avenet et al., "Transduction in Taste Receptor Cells Requires cAMP–dependent Protein Kinase," *Nature* 331–4 (1988).

Axelsson et al., "The Influence of Dietary Nucleotides on Erythrocyte Membrane Fatty Acids and Plasma Lipids in Preterm Infants," *Acta Paediatr*. 86)5:539–44 (1997).

Bartoshuk, "Taste Mixtures: Is Mixture Suppression Related to Compression!, " *Physiol. Behav*. 14:643–9 (1975).

Béhé et al., "Membrane Currents in Taste Cells of the Rat Fungiform Papilla," *J. Gen. Physiol*. 96:1061–84 (1990).

Benedetti et al., "Sweet and Bitter Taste: Structure and Conformations of Two Aspartame Dipeptide Analogues," *J. Pept. Sci*. 1:349–59 (1995).

Bernhardt et al., "Changes in $IP_3$ and Cytosolic $Ca^{2+}$ in Response to Sugars and Non–sugar Sweeteners in Transduction of Sweet Taste in the Rat," *J. Physiol*. 490(2):325–26 (1996).

Birnbaumer et al., "Receptor–effector Coupling by G Proteins," *Biochem. Biophys. Acta* 1031:163–224 (1990).

Birnbaumer, "G Proteins in Signal Transduction," *Ann. Rev. Pharmacol. Toxicol*. 30:675–705 (1990).

Bruch & Kalinoski, "Interaction of GTP–binding Regulatory Proteins with Chemosensory Receptors," *J. Biol. Chem*. 262(5):2401–4 (1987).

Bubis & Khorana, "Sites of Interaction in the Complex Between β–and γ–Subunits of Transducin," *J. Biol. Chem*. 265(22):12995–9 (1990).

Cagan & Morris, "Biochemical Studies of Taste Sensation: Binding to Taste Tissue of $^3$H–Labeled Monellin, a Sweet–tasting Protein," *Proc. Nat'l Acad. Sci. USA*. 76(4):1692–6 (1979).

Cane et al., "Harnessing the Biosynthetic Code: Combinations, Permutations, and Mutations," *Science* 282(5386):63–68 (1998).

Capecchi, "Altering the Genome by Homologous Recombination," *Science* 244(4910):1288–92 (1989).

Cheung et al., "Specific Activation of $G_s$ by Synthetic Peptides Corresponding to an Intracellular Loop of the β–Adrenergic Receptor," *FEBS Lett*. 279(2):277–80 (1991).

Cummings et al., "Sweet Taste Transduction in Hamster: Sweeteners and Cyclic Nucleotides Depolarize Taste Cells by Reducing a $K^{30}$ Current," *J. Neurophysiol*. 75(3):1256–63 (1996).

Drewnowski et al., "Taste Responses and Preferences for Sweet High–fat Foods: Evidence for Opioid Involvement," *Physiol. Behav*. 51:371–9 (1992).

Dum et al., "Activation of Hypothalamic β–Endorphin Pools by Reward Induced by Highly Palatable Food," *Pharmacol. Biochem. Behav*. 18:443–7 (1983).

Formaker & Frank, "Responses of the Hamster Chorda Tympani Nerve to Binary Component Taste Stimuli: Evidence for Peripheral Gustatory Mixture Interactions," *Brain Res*. 727:79–90 (1996).

Fung & Nash, "Characterization of Transducin from Bovine Retinal Rod Outer Segments," *J. Biol. Chem*. 258(17):10503–10 (1983).

Fung et al., "Flow of Information in the Light–triggered Cyclic Nucleotide Cascade of Vision," *Proc. Nat'l Acad. Sci. USA* 78(1): 152–6 (1981).

Gilbertson et al., "Proton Currents Through Amiloride–sensitive Na Channels in Hamster Taste Cells," *J. Gen. Physiol*. 100(5):803–24 (1992).

Gilbertson, "Gustatory Mechanisms for the Detection of Fat," *Curr. Opin. Neurobiol*. 8:447–52 (1998).

Gillespie, "Phosphodiesterases in Visual Transduction by Rods and Cones," *in* Cyclic Nucleotide Phosphodiesterases: Structure, Regulation and Drug Action 163–84 (Joe Beavo & Miles D. Houslay eds., 1990).

Glendinning, "Is the Bitter Rejection Response Always Adaptive!," *Physiol. Behav*.56(6): 1217–27 (1994).

Greenberg et al., "Stimulation of Neuronal Acetylcholine Receptors Induces Rapid Gene Transcription," *Science* 234:80–3 (1986).

Gilbertson et al., "Fatty Acid Modulation of $K^+$ Channels in Taste Receptor Cells: Gustatory Cues for Dietary Fat," *Am. J. Physiol*. 272:C1203–C1210 (1997).

Halliday et al., "Limited Trypsin Proteolysis of Photoreceptor GTP–binding Protein," *J. Biol. Chem*. 259(1):516–25 (1984).

Hamm et al., "Site of G Protein Binding to Rhodopsin Mapped with Synthetic Peptides from the α Subunit," *Science* 241(4867):832–5 (1988).

Heck et al., "Salt Taste Transduction Occurs Through an Amiloride–sensitive Sodium Transport Pathway, " *Science* 223:403–5 (1984).

Herness & Gilbertson, "Cellular Mechanisms of Taste Transduction," *Ann. Rev. Physiol*. 61:873–900 (1999).

Higginbotham et al., "Flavour Potentiating Properties of Talin Sweetener (Thuamatin)," *in* The Quality of Foods and Beverages 91–111 (George E. Inglett ed., 1981).

Hoon et al., "Functional Expression of the Taste Specific G–protein, α–Gustducin," *Biochem. J*. 309–629–36 (1995).

Houghten et al., "Generation and Use of Synthetic Peptide Combinatorial Libraries for Basic Research and Drug Discovery," *Nature* 354(6348):84–6 (1991).

Jones & Reed, "$G_{olf}$: An Olfactory Neuron Specific–G Protein Involved in Odorant Signal Transduction," *Science* 244(4906):790–5 (1989).
Kakkar et al., "Calmodulin–dependent Cyclic Nucleotide Phosphodiesterase (PDEI)," *Cell Mol. Life Sci.* 55(8–9):1164–86 (1999).
Kinnamon & Roper, "Membrane Properties of Isolated Mudpuppy Taste Cells," *J. Gen. Physiol.* 91:351–71 (1988).
Kinnamon et al., "Apical Localization of $K^+$ Channels in Taste Cells Provides the Basis for Sour Taste Transduction," *Proc. Nat'l Acad. Sci. USA* 85:7023–7 (1988).
Kinnamon, "Taste Transduction: A Diversity of Mechanisms," *Trends. Neurosci.* 11(11):491–6 (1988).
Kolesnikov & Margolskee, "A Cyclic–nucleotide–suppressible Conductance Activated by Transducinin Taste Cells," *Nature* 376(6535): 85–8 (1995).
Komuro & Rakic, "Orchestration of Neuronal Migration by Activity of Ion Channels, Neurotransmitter Receptors, and Intracellular $Ca^{2+}$ Fluctuations," *J. Neurobiol.* 37(1):110–30 (1998).
König et al., "Three Cytoplasmic Loops of Rhodopsin Interact with Transducin," *Proc. Nat'l Acad. Sci. USA* 86:6878–82 (1989).
Krieg & Melton, "*In Vitro* RNA Synthesis with SP6 RNA Polymerase," *Methods Enzymol.* 155:397–415 (1987).
Kurihara & Koyama, "High Activity of Adenyl Cyclase in Olfactory and Gustatory Organs," *Biochem. Biophys. Res. Commun.* 48(1):30–4 (1972).
Laemmli, "Cleavage of Structural Proteins During the Assembly of the Head of Bacteriophage T4," *Nature* 227:680–5 (1970).
Lam et al., "A New Type of Synthetic Peptide Library for Identifying Ligand–binding Activity," *Nature* 354(6348):82–84 (1991).
Lee, "The Chemistry and Biochemistry of the Sweetness of Sugars," *in* 45 Advances in Carbohydrate Chemistry and Biochemistry 199–351 (1987).
Lerea et al., "Identification of Specific Transducin αSubunits in Retinal Rod and Cone Photoreceptors," *Science* 234(4772):77–80 (1986).
Lochrie et al., "Sequence of the Alpha Subunit of Photoreceptor G Protein: Homologies Between Transducin, *ras*, and Elongation Factors," *Science* 228:96–9 (1985).
Margolskee, "The Biochemistry and Molecular Biology Taste Transduction," *Curr. Opin. Neurobiol.* 3(4):526–31 (1993).
Margolskee, "The Molecular Biology of Taste Transduction," *BioEssays* 15(10):645–50 (1993).
Mazzoni et al., "Structural Analysis of Rod GTP–binding Protein, $G_t$, "*J. Biol. Chem.* 266(21):14072–81 (1991).
McLaughlin et al., Abstract 184, "Gustducin: A Tasteful G Protein," *Chem. Senses* 17(5):667 (1992).
Medynski et al., "Amino Acid Sequence of the α Subunit of Transducin Deduced from the cDNA Sequence," *Proc. Nat'l Acad. Sci. USA* 82(13):4311–5 (1985).
Mirenowicz & Schultz, "Preferential Activation of Midbrain Dopamine Neurons by Appetitive Rather than Aversive Stimuli," *Nature* 379:449–51 (1996).
Morton, "Sour Orange," *in* Fruits of Warm Climates 130–3 (1987) *at* http://www.hort.purdue.edu/newcrop/morton/sour_orange.html (last accessed Jun. 21, 2007).
Navon & Fung, "Characterization of Transducin from Bovine Retinal Rod Outer Segments," *J. Biol. Chem.* 263(1):489–96 (1988).
Neer et al., "Analysis of G–protein α and βγ Subunits by *in Vitro* Translation," *Methods Enzymol*, 237:226–39 (1994).
Ninomiya et al., "Gustatory Neural Responses in Three Different Strains of Mice," *Brain Res.* 302(2):305–14 (1984).
Ninomiya et al., "Lack of Gurmarin Sensitivity of Sweet Taste of Receptors Innervated by the Glossopharyngeal Nerve in C57BL Mice," *Am. J. Physiol.* 272 (3 Pt 2):R1002–R1006 (1997).
Peterson, "A Simplification of the Protein Assay Method of Lowry *et al.*, Which Is More Generally Applicable," *Anal. Biochem.* 83(2):346–56 (1977).
Price, "Phosphodiesterase in Tongue Epithelium: Activation by Bitter Taste Stimuli," *Nature*. 241:54–5 (1973).
Rahmatullah et al., "Specificity of G Protein α–γ Subunit Interactions, " *J. Biol. Chem.* 270(7):2946–51 (1995).
Raintree Nutrition Inc., "Database File for: Bitter Orange (*Citrus aurantium*)," *Tropical Plant Database*, http://www.rain–tree.com/orange.htm (1996) (last accessed Jun. 21, 2007).
Rarick et al., "A Site on Rod G Protein α Subunit That Mediates Effector Activation," *Science* 256:1031–3 (1992).
Rodbell et al., "The Glucagon–sensitive Adenyl Cyclase System in Plasma Membranes of Rat Liver. V. An Obligatory Role of Guanylnucleotides in Glucagon Action," *J. Biol. Chem.* 246(6):1877–82 (1971).
Roper, "The Cell Biology of Vertebrate Taste Receptors," *Ann. Rev. Neurosci.* 12–:329–53 (1989).
Roy, "A Review of Sweet Taste Potentiation Brought About by Divalent Oxygen and Sulfur Incorporation," *Crit. Rev. Food Sci. Nutr.* 31(1/2):59–77 (1992).
Schiffman & Gatlin, "Sweeteners: State of Knowledge Review," *Neurosci. Biobehav. Rev.* 17:313–45 (1993).
Schiffman et al., "Amiloride Reduces the Taste Intensity of $Na^+$ and $Li^+$ Salts and Sweeteners," *Proc. Nat'l Acad. Sci. USA* 80:6136–40 (1983).
Schmidt et al., "Specificity of G Protein αand γ Subunit Interactions," *J. Biol. Chem.* 267(20):13807–10 (1992).
Scott & Smith, "Searching for Peptide Ligands with an Epitope Library," *Science*249(4967):386–90 (1990).
Shimazaki et al., "Photoaffinity Labeling of Thuamatin–binding Protein in Monkey Circumvallate Papillae," *Biochim. Biophys. Acta* 884:291–8 (1986).
Shin et al., "Structure–Taste Correlations in Sweet Dihydrochalcone, Sweet Dihydroisocoumarin, and Bitter Flavone Compounds," *J. Med. Chem.* 38(21):4325–31 (1995).
Simon et al., "Diversity of G Proteins in Signal Transduction," *Science* 252:802–8 (1991).
Sonnenburg et al., "Identification, Quantitation, and Cellular Localization of PDE1 Calmodulin–stimulated Cyclic Nucleotide Phosphodiesterases," *Methods* 14(1):3–19 (1998).
Spielman, et al., "A Rapid Method of Collecting Taste Tissue from Rats and Mice," *Chem. Senses* 14(6):841–6 (1989).
Strathmann et al., "Diversity of the G–protein Family: Sequences from Five Additional α Subunits in the Mouse," *Proc. Nat'l Acad. Sci. USA* 86:7407–9 (1989).
Striem et al., "Sweet Tastants Stimulate Adenylate Cyclase Coupled to GTP–binding Protein in Rat Tongue Membranes," *Biochem. J.* 260:121–6 (1989).
Stryer & Bourne, "G Proteins: A Family of Signal Transducers," *Annu. Rev. Cell Biol.* 2:391–419 (1986).
Sugawara et al., "Profile of Nucleotides and Nucleosides of Human Milk," *J. Nutr. Sci. Vitaminol.* 41(4):409–18 (1995).

Takami et al., "Human Taste Cells Express the G Protein α–Gustducin and Neuron–specific Enolase," *Mol.Brain Res*. 22(1–4):193–203 (1994).

Tam, "Synthetic Peptide Vaccine Design: Synthesis and Properties of a High–Density Multiple Antigenic Peptide System," *Proc. Nat'l Acad. Sci. USA* 85:5409–13 (1988).

Tanabe et al., "Primary Structure of the α–Subunit of Transducin and Its Relationship to *ras* Proteins," *Nature* 315(6016):242–5 (1985).

Tareilus et al., "Approaches for Monitoring Rapid Kinetics of Second Messenger Signaling," *in* Current Techniques & Protocols 193–202 (1995).

Thomas et al., "Identification of Synaptophysin as a Hexameric Channel Protein of the Synaptic Vesicle Membrane," *Science* 242(4881):1050–3 (1988).

Tonosaki & Funakoshi, "Cyclic Nucleotides May Mediate Taste Transduction," *Nature* 331:354–6 (1988).

Tsunenari et al., "Activaton by Bitter Substances of a Cationic Channel in Membrane Patches Excised from the Bullfrog Taste Receptor Cell," *J. Physiol*. 519(2):397–404 (1999).

Weishaar et al., "A New Generation of Phosphodiesterase Inhibitors: Multiple Molecular Forms of Phosphodiesterase and the Potential for Drug Selectivity," *J. Med. Chem*. 28(5):537–45 (1985).

Wong et al., "Biochemical and Transgenic Analysis of Gustaducin's Role in Bitter and Sweet Transduction," *in* LXI Cold Spring Harbor Symposia on Quantitative Biology 173–84 (1996).

Yatsunami & Khorana, "GTPase of Bovine Rod Outer Segments: The Amino Acid Sequence of the α Subunit as Derived from the cDNA Sequence," *Proc. Nat'l Acad. Sci. USA* 82:4316–20 (1985).

* cited by examiner

INHIBITORS OF THE BITTER TASTE RESPONSE

Matter enclosed in heavy brackets [ ] appears in the original patent but forms no part of this reissue specification; matter printed in italics indicates the additions made by reissue.

This application claims priority to U.S. Provisional Application No. 60/113,562, filed Dec. 23, 1998.

This research was supported by National Institutes of Health Grants RO1DC03055 and RO1DC3155, so that the United States Government has certain rights herein.

1. INTRODUCTION

The present invention relates to methods for identifying inhibitors of the bitter taste response, and by methods of using such inhibitors to either block the perception of bitterness and/or promote the perception of a sweet taste. The inhibitors of the invention may be used as flavor enhancers in foods and pharmaceuticals. The methods of the invention may further be used to characterize the gustatory perception of novel tastants.

2. BACKGROUND OF THE INVENTION

The sensation of taste has profound biological significance. It has much wider ramifications than merely providing mankind with pleasurable culinary experiences. Taste conveys numerous biological cues to humans and other animals, identifying tainted or spoiled foods and providing hedonic responses which may be proportionate to caloric or nutritive value.

There are generally considered to be only four or five categories of basic taste: sweet, sour, bitter, acid, and "umami" (the Japanese word describing the taste of monosodium glutamate; Hemess, M. S. & Gilbertson, T. A., 1999, Annu. Rev. Physiol. 61:873–900). These can be subclassified as the appetitive tastes, such as salty, sweet and umami, which are associated with nutrient-containing foods, and the bitter and sour tastes elicited by toxic compounds. The latter two produce an aversive reaction which may protect an organism by discouraging the ingestion of unhealthy or dangerous foods. Among the undesirable compounds associated with a bitter taste are plant alkaloids such as caffeine, strychnine and quinine, cyanide, and metabolic waste products such as urea (Lindemann, B., 1996, Physiol. Rev. 76:719–766). It has recently been suggested that fat, the most energy-dense nutrient, may possess gustatory cues (Id., citing Gilbertson T. A. et al., 1997, Am. J. Physiol. 272:C1203–1210 and Gilbertson, T. A., 1998, Curr. Opin. Neurobiol. 8:447–452).

The anatomic basis for the initial events of taste is the taste receptor cell ("TRC"), located in clusters referred to as "taste buds" (Lindemann, supra). Taste buds are distributed throughout the oral cavity, including the tongue as well as extra-lingual locations (see Hemess and Gilbertson). In the human tongue, taste buds are organized into three specialized types of specialized structures, namely fungiform, foliate, and circumvallate papillae. Each taste bud comprises between about 50 and 100 individual cells grouped into a cluster that is between 20 and 40 microns in diameter. Nerve fibers enter from the base of the taste bud and synapse onto some of the taste receptor cells. Typically, a single TRC contacts several sensory nerve fibers, and each sensory fiber innervates several TRCs in the same taste bud (Lindemann, supra).

When a subject ingests a tastant, and that tastant encounters a taste receptor cell in the appropriate concentration, an action potential is produced which, via synapses with primary sensory neurons, communicates the signal registered by the receptor, via afferent nerves, to the appropriate region of the sensory cortex of the brain, resulting in the perception of a particular taste by the subject. Food appraisal can give rise to a hedonic response involving the activation of midbrain dopamine neurons (Lindemann, supra, citing Mirenowicz, J. & Schultz, W., 1996, Nature (London) 379:449–451) and the release of endogenous opiates (Lindemann, supra, citing Drenowski, A., et al., 1992, Physiol. Behav. 51:371–379; Dum, J. et al., 1983, Pharmacol. Biochem. Behav. 18:443–447).

Much research has been directed toward elucidating the physiology of taste. TRCs of most, if not all, vertebrate species possess voltage-gated sodium, potassium, and calcium ion channels with properties similar to those of neurons (Kinnamon, S. C. & Margolskee, R. F., 1996, Curr. Opin. Neurobiol. 6:506–513). Different types of primary tastes appear to utilize different types of transduction mechanisms, and certain types of tastes may employ multiple mechanisms which may reflect varying nutritional requirements amongst species (Kinnamon & Margolskee, supra). For example, in the hamster, acid taste is associated with the influx of protons through an amiloride-sensitive sodium ion channel (Id., citing Gilbertson, T. A. et al., 1993, Neuron 10:931–942), whereas in the mudpuppy, a proton block of potassium ion channels at the apical cell membrane is involved (Kinnamon & Margolskee, supra, citing Kinnamon, S. C. et al., 1988, Proc. Natl. Acad. Sci. U.S.A. 85:7023–7027). Salty taste is typically transduced via permeation of sodium ions through amiloride-sensitive sodium channels.

Sweet taste has been associated with a second messenger system which may differ depending upon whether the tastant is a natural or artificial sweetener, the former believed to utilize cAMP, the latter inositol trisphosphate ($IP_3$; Hemess M. S. & Gilbertson, T. A., 1999, Annu. Rev. Physiol. 61:873–900). There is evidence that a membrane-bound receptor, such as that involved in the activation of $G_s$ and adenylyl cyclase, may be involved in the perception of sweet tastes (Id.).

Bitter taste sensations are also thought to involve cAMP and $IP_3$ (Kinnamon & Margolskee, supra). The bitter compound denatonium causes calcium ion release from rat TRCs and the rapid elevation of $IP_3$ levels in rodent taste tissue (Id., citing Bernhardt, S J. et al., 1996, J. Physiol. (London) 490:325–336 and Akabas, M. H., et al., 1988, Science 242:1047–1050). Since denatonium cannot pass the cell membrane, it has been suggested that it may activate G-protein-coupled receptors, whereby the $\alpha$ and/or $\beta\gamma$ G protein subunits would activate phospholipase C, leading to $IP_3$ generation and the release of calcium ions (Kinnamon & Margolskee, supra).

In recent years, a taste-specific G protein termed "gustducin", which is homologous to the retinal G protein, transducin, has been cloned and characterized (Id., citing McLaughlin, S. et al., 1992, Nature (London) 357:563–569). Mice in which the a gustducin gene has been knocked out exhibit diminished responses to certain bitter (and certain sweet) tastants, suggesting that gustducin may regulate the TRC $IP_3$ response (Kinnamon & Margolskee, citing Wong, G. T. et al., 1996, Nature (London) 381:796–800). Introducing a wild-type rat $\alpha$-gustducin-encoding cDNA into $\alpha$-gustducin null mice restored their responsiveness to bitter and sweet compounds (Ming, D. et al., 1998, Proc. Natl. Acad. Sci. U.S.A. 95:8933–8938, citing Wong, G. T., et al., 1996, Cold Spring Harbor Symp. Quant. Biol. 61:173–184). Gustducin's γ subunit ($\gamma_{13}$) has recently been shown to mediate activation of phospholipase C in response to the bitter compound denatonium (Huang, L. et al., 1999, Nature Neurosci. 2:1055–1062).

Although it had been believed that rod and cone transducins were specific G proteins present only in photoreceptor cells of the vertebrate retina (Lochrie, M. A. et al., 1985, Science 228:96–99; Medynski, D. C. et al., 1985, Proc. Natl. Acad. Sci. U.S.A. 82:4311–4315; Tanabe, T. et al., 1985, Nature (London) 315:242–245; Yatsunami K. & Khorana, H. G., 1985, Proc. Natl. Acad. Sci. U.S.A. 82:4316–4320), it was discovered that od transducin is also present in vertebrate taste cells, where it specifically activates a phosphodiesterase isolated from taste tissue (Ruiz-Avila, L. et al., 1995, Nature (London) 376:80–85). Using a trypsin-sensitivity assay, it was demonstrated that the bitter compound denatonium, in the presence of taste cell membranes, activates transducin but not the G-protein, $G_i$ (Id.). This activation could be inhibited by a peptide derived from the C-terminal region of transducin, which competitively inhibits the rhodopsin-transducin interaction (Id. and Hamm, H. E., et al., 1988, Science 241:832–8359). Ruiz-Avila et al. (supra) proposed that transducin may be involved in bitter taste transduction via a cascade similar to that which occurs in visual perception, whereby a stimulated bitter receptor may activate taste-cell transducin, which in turn activates phosphodiesterase. The activated phosphodiesterase may then decrease levels of intracellular 3',5'-cyclic nucleotides, and the resulting lower levels of cyclic nucleotides could lead to TRC depolarization by a mechanism referred to as "cyclic-nucleotide-suppressible conductance"(Id. citing Kolesnikov, S. & Margolskee, R. F., 1995, Nature (London) 376:85–88).

More recently, Ming, D. et al., 1998, Proc. Natl. Acad. Sci. U.S.A. 95:8933–8938 reported that both gustducin and transducin, in the presence of bovine taste cell membranes, were specifically activated by a number of bitter compounds, including denatonium, quinine, and strychnine. This activation was found to depend upon an interaction with the C-terminus of gustducin and required the presence of G-protein βγ subunits; it could be competitively inhibited by peptides derived from the sites of interaction of rhodopsin and transducin.

SUMMARY OF THE INVENTION

The present invention relates to methods for identifying compounds which inhibit the sensory perception of bitterness. It is based, at least in part, on the discovery that adenosine monophosphate (AMP) and related compounds inhibited the activation of transducin by bitter tastant-stimulated taste receptors, decreased neuronal stimulation by said tastants, and resulted in behavioral responses which indicate that the sensation of bitterness was greatly diminished.

Inhibitors of the invention may be used to decrease or abrogate the perception of bitterness of bitter tastants, in which capacity they are referred to as "bitterness inhibitors". In related embodiments, the present invention provides for methods of decreasing the perception of bitterness associated with a tastant by co-administering one or more bitterness inhibitors, and also provides for compositions comprising a bitter tastant and a bitterness inhibitor.

Inhibitors of the invention may also be found to convey a perception of sweetness when they are present with or without other tastants; in this capacity, they are referred to as "inhibitor sweeteners". In various embodiments, the present invention provides for methods of creating the perception of sweetness, in which an inhibitor sweeter is administered to a subject, and also provides for compositions comprising inhibitor sweeteners.

The inhibitors of the invention may be used to enhance the flavor of foods, beverages, and pharmaceuticals by decreasing or eliminating bitter taste features. In addition to increasing food consumer satisfaction, inhibitors of the invention may also permit the incorporation, into foods and pharmaceuticals, of bitter tastants that improve shelf-life or nutritive value. The inhibitors of the invention could increase food intake in humans or livestock. Moreover, inhibitors of the invention could render medical procedures involving bitter compositions more palatable, and improve compliance in drug regimens involving bitter tastants, particularly when administered to children.

In further embodiments, the present invention provides for methods for identifying and/or characterizing bitter tastants which evoke taste responses similar to those of known bitter compounds. Non-toxic bitter compounds identified in this manner could be used as additives to provoke a desired aversive response—for example, to discourage ingestion of compositions containing these compounds by children or animals.

4. DESCRIPTION OF THE FIGURES

FIGS. 1A–E. AMP inhibits activation of transducin by bitter stimuli in the presence of bovine taste receptor cell membranes. (A) Inactive (GDP-bound) transducin (rightmost lane) generates a 23 kDa fragment on digestion with trypsin. Active (GTP-γS-bound) transducin (second from right lane) activated by DEN plus taste membranes generates a 32-kDa fragment on treatment with trypsin. Increasing concentrations of AMP (0.25, 0.5, 1.25, 2.5, and 5.0 mM) inhibit activation of transducin by DEN plus bovine taste receptor membranes. as determined by the shift from 32-kDa to 23-kDa fragments. (B) Increasing concentrations of AMP (0.01, 0.05, 0.10, 0.50, 1.0, 1.5, 2.0, and 2.5 mM) inhibit activation of transducin by 1.0 mM QUI plus bovine taste membranes. (C) AMP (2.5 mM) inhibits the taste membrane-dependant activation of transducin by DEN (5.0 mM), QUI (1.0 mM), strychnine hydrochloride (STR, 5.0 mM), nicotine hemisulfate (NIC, 5.0 mM), and atropine hydrochloride (ATR, 5.0 mM). (D) AMP (0.25, 0.5, 1.25, 2.5, and 5.0 mM) does not inhibit activation of transducin by 0.001 mM rhodopsin. (E) GMP (0.25, 0.5, 1.25, 2.5, and 5.0 mM) does not inhibit activation of transducin by DEN (5.0 mM) plus bovine taste membranes.

Figure 2:
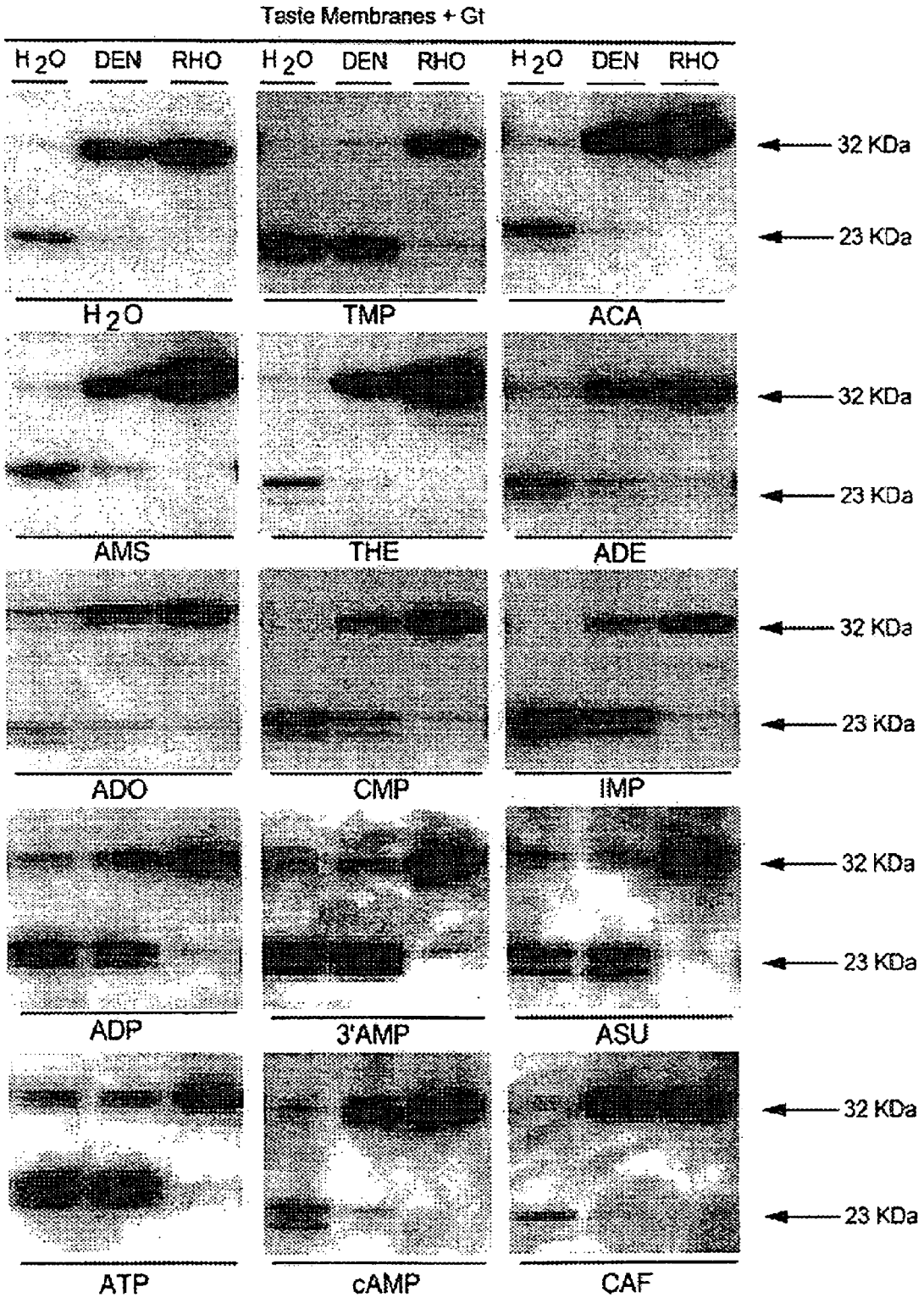

FIG. 2. Only certain AMP analogues block activation of transducin by DEN plus taste membranes. Taste membrane-dependent activation of transducin by DEN (5.0 mM) is not inhibited by adenosine 5'-carboxylate (ACA, 5.0 mM). adenosine 5'-monosulfate (AMS, 5.0 mM), theophylline (THE, 5.0 mM), adenine hydrochloride (ADE, 5.0 mM). adenosine hydrochloride (ADO. 5.0 mM), cAMP (5.0 mM), or caffeine (CAF, 5.0 mM). DEN/taste membrane activation of transducin is inhibited by thymidine 5'-monophosphate (TMP, 5.0 mM), 5'-cytidylic acid (CMP, 5.0 mM), inosinic acid (IMP, 5.0 mM), ADP (5.0 mM), 3'AMP (5.0 mM), adenosine 5'-succinate (ASU, 5.0 mM) and ATP (5.0 mM). $H_2O$ and rhodopsin (RHO) lanes control for nonspecific receptor-independent effects.

FIGS. 3A–E. AMP blocks aversive responses of mice to several bitter compounds. (A) Forty-eight-hour two-bottle preference responses of C57BL/6J mice (n=10) to DEN alone, AMP alone, DEN plus AMP (0.1 and 1.0 mM), and DEN plus GMP (0.1 and 1.0 mM). AMP (0.1 and 1.0 mM) inhibited the aversive responses to DEN at 0.05, 0.10, 0.50, and 1.0 mM (P<0.001). GMP (0.1 and 1.0 mM) did not inhibit the aversive responses to DEN. P<0.001. (B) Increasing concentrations of AMP (0.1, 1.0, 5.0 mM) shifted the dose-aversiveness curve to the right. AMP alone did not elicit behavioral responses until its concentration reached 0.5 mM. (C) Preference responses of C57BL/6J mice (n=10) to QUI alone, AMP alone, QUI plus AMP (0.1 and 0.5 mM), and QUI plus GMP (0.1 and 0.5 mM). AMP (0.1 and 0.5 mM) inhibited the aversive responses to QUI at 0.05, 0.10, and 0.50 mM (P<0.001). GMP (0.1 and 0.5 mM) did not inhibit the aversive responses to QUI P<0.001. (D) Increasing concentrations of AMP shifted the dose-aversiveness curve to the right. (E) Preference responses of C57BL/6J mice (n=10) exposed to two different concentrations of tastants±0.1 mM AMP. AMP inhibited the aversive responses to the bitter tastants sparteine (SPA) at 0.05 and 0.10 mM (P<0.001): and (−)-epicatechin (E.I.) at 0.05 mM and 0.10 mM (P<0.01); AMP did not alter the behavioral responses to NaCl (0.1 and 0.3 M), HCl (0.01 and 0.10 mM), sucrose (SUC) (5.0 and 150 mM), or the high-potency artificial sweetener SC45647 (SC) (0.01 and 0.10 mM). **P<0.001, *P<0.01.

FIGS. 4A–I. AMP diminishes the glossopharyngeal nerve responses of mice to lingual stimulation with bitter tastants. (A) Glossopharyngeal responses to 0.1 M $NH_4Cl$, 5.0 mM DEN, 1.0 mM sparteine (SPA), 1.0 mM strychnine (STR), and 1.0 mM atropine (ATR). (B) Glossopharyngeal responses to the above compounds mixed with 0.1 mM AMP. (C) Glossopharyngeal responses to the above compounds mixed with 0.1 mM GMP. (D) Glossopharyngeal responses to a series of concentrations of AMP (0.01, 0.1, 1.0, 5.0 mM) alone and in combination with QUI (0.1 mM and 1.0 mM) (E and F, respectively). (G) Relative tonic responses recorded from glossopharyngeal nerves of mice (n=5 to 7) stimulated by lingual application of DEN (0.1, 0.5, 1.0, 5.0, and 10.0 mM)±AMP (0.1 and 1.0 mM). **P<0.001; *P<0.01. (H) Relative tonic responses recorded from glossopharyngeal nerves of mice (n=6 to 8) stimulated by lingual application of QUI (0.1, 0.3, and 1.0 mM) and its mixtures with AMP (0.1 and 1.0 mM). P<0.001. (I) Relative tonic responses recorded from glossopharyngeal nerves of mice (n=4 to 7) stimulated by lingual application of 5.0 mM HCl, 0.1 M NaCl, 3.0 mM SC45647, 0.5 M sucrose (SUC), 1.0 mM SPA, or water with or without 0.1 mM AMP. AMP inhibits the relative tonic responses of 1.0 mM SPA (P<0.001) and 3.0 mM SC45647 (P<0.01), but not of the other compounds. P<0.001; *P<0.01.

5. DETAILED DESCRIPTION OF THE INVENTION

For purposes of clarity of presentation, and not by way of limitation, the detailed description of the invention is divided into the following subsections:

(a) methods of identifying inhibitors;

(b) compositions containing inhibitors and their uses; and (c) identifying bitter tastants.

5.1 Methods of Identifying Inhibitors

The present invention provides for methods for identifying an inhibitor of bitter taste comprising (i) contacting a taste receptor with a G-protein, selected from the group consisting of transducin and gustducin, and a bitter tastant, under conditions suitable for activation of the G-protein by the bitter tastant, and measuring the level of G-protein activation; (ii) in a separate experiment, contacting a taste receptor with a G-protein selected from the group consisting of transducin and gustducin, the bitter tastant, and a test inhibitor, and measuring the level of G-protein activation, where the G-protein is the same as that used in part (i), where the conditions are essentially the same as in part (i), and then (iii) comparing the level of activation of the G-protein measured in part (i) with the level of activation of the G-protein measured in part (ii), wherein a lower level of activated G-protein in the presence of the test inhibitor has a positive correlation with an ability of the test inhibitor to inhibit the perception of a bitter taste associated with the tastant.

The foregoing methods may be practiced in vivo or in vitro.

The taste receptor and G-protein may be derived from the same species of animal or different species. In preferred but non-limiting embodiments, the source of taste receptor and G-protein is (are) a mammal(s).

The term "taste receptor", as used herein is defined as a molecule or molecular complex which occurs in the membrane of a taste receptor cell and which acts in transducing responses to bitter or sweet tastants. The taste receptor may be comprised in a living cell or may be part of a cell or tissue extract; it need not be isolated from other molecules or tissue elements. In specific non-limiting embodiments, it is comprised in a membrane preparation derived from taste receptor cells, for example, as described infra and in Section 6. The taste receptor may be native protein or reconstituted from recombinant clones.

The term "transducin" refers to a multimeric, preferably heterotrimeric, molecule comprising an α-transducin unit as contained, for example, in a transducin heterotrimeric molecule found in rod cells of the retina and/or taste receptor cells, as described, for example, in Ming, D. et al., 1998, Proc. Natl. Sci. U.S.A. 95:8933–8938. In non-limiting embodiments, the transducin molecule may further comprise a β subunit and a γ subunit, for example in the form of a combined βγ subunit, as found in native heterotrimeric transducin or another heterotrimeric G-protein molecule, such as native heterotrimeric gustducin. The nucleotide and/or amino acid sequences of several transducin genes and proteins are known, and are set forth in, for example, Medynski, D. C., et al., 1985, Proc. Natl. Acad. Sci. U.S.A. 82:4311–4315 and Tanabe, T., et al., 1985, Nature (London) 315:242–245. For use in the methods of the invention, transducin may be purified from a natural source or obtained by recombinant expression using known techniques.

The term "gustducin" refers to a multimeric, preferably heterotrimeric, molecule comprising an α-gustducin unit as contained, for example, in a gustducin heterotrimeric molecule found in taste receptor cells and/or chemoreceptive cells of the stomach and duodenum, as described, for example, in papers describing the original cloning of gustducin, such as McLaughlin, S. K., et al., 1992, Nature (London) 357:563–569; McLaughlin, S. K., et al., 1993, in "The Molecular Basis of Smell and Taste Transduction", CIBA Foundation Symposium 179, Chadwick, D. et al., eds., Chichester, UK: Wiley, pp. 186–200; and McLaughlin, S. K., et al., 1994, Physiol. Behav. 56:1157–1164. In non-limiting embodiments, the gustducin molecule may further comprise a β subunit and a γ subunit, for example in the form of a combined βγ subunit, as found in native heterotrimeric gustducin or another heterotrimeric G-protein molecule, such as transducin. Additional nucleotide and/or amino acid sequences of gustducin genes as set forth in, for example, Ming, D. et al., 1998, Proc. Natl. Acad. Sci. U.S.A. 95:8933–8938 and Huang, L. et al., 1999, Nature Neurosci. 2:1055–1062. For use in the methods of the invention, gustducin may be purified from a natural source of obtained by recombinant expression using known techniques.

A "bitter tastant", as defined herein, is a compound or molecular complex that induces, in a subject, the perception of a bitter taste. In particular, a bitter tastant is one which results in the activation of gustducin and/or transducin, for example, but not by way of limitation, in an assay such as that described in Ming, D. et al., 1998, Proc. Natl. Sci. U.S.A. 95:8933–8938 (e.g., see FIG. 3 of that reference). Examples of bitter tastants include but are not limited to denatonium benzoate ("denatonium"; also "DEN"), quinine hydrochloride ("quinine"; also "QUI"), strychnine hydrochloride ("strychnine"; also "STR"), nicotine hemisulfate ("nicotine"; also "NIC"), atropine hydrochloride ("atropine"; also "ATR"), sparteine, naringin, caffeic acid ("caffeine"; also "CAF"), quinacrine, and epicatechin. See Ming et al., 1999, Proc. Natl. Acad. Sci. U.S.A. 96:9903–9908, incorporated by reference herein.

The phrase "conditions suitable for activation of the G-protein by the bitter tastant" refers to conditions under which the combination of elements, namely taste receptor, G-protein, and bitter tastant, in the absence of an inhibitor, result in G-protein activation. Examples of suitable conditions include those which occur in vivo in a taste receptor cell, or in vitro conditions which approximate those found in vivo including approximately neutral pH values (e.g., pH 6.5–8.5), and salt concentrations equivalent to 50–150 mM NaCl.

Virtually any compound may be tested for its ability to inhibit bitter taste transduction and thus qualify as a "test inhibitor". For example, peptides, peptidomimetics, carbohydrates, glycoproteins, lipids, fatty acids, nucleic acids, and combinations of these elements may be tested. Non-limiting examples of preferred inhibitors for testing (those more likely to be successful inhibitors) are structural homologs of adenosine 5' monophosphate ("AMP"). Such structural homologs are defined as compounds which comprise a sugar moiety, a nucleoside base, preferably adenine or an adenine derivative, preferably not guanine, and an anionic organic molecule for example, but not by way of limitation, selected from the group consisting of phosphates and their derivatives, sulfates and their derivatives, and succinate and its derivatives. Not all such molecules may be effective inhibitors, but would qualify as preferred "test inhibitors". It may be particularly desirable to test compounds structurally related to the following compounds, which have been demonstrated to successfully inhibit bitter taste transduction as measured by G-protein activation: thymidine 5' monophosphate, adenosine 5' diphosphate, adenosine 3' monophospate (3'-AMP), adenosine 5'-succinate, adenosine 5' triphosphate ("ATP"), adenosine 2' monophosphate, 5'-cytidylic acid, and inosinic acid.

In the methods of the invention, it may be desirable to vary the amount of bitter tastant and/or test inhibitor in order to demonstrate inhibition or lack thereof and to quantify potency. Naturally occurring bitter tastants are typically active in the range of 10–500 mM, but particularly potent tastants may be detectable at concentrations as low as 100–100 nM. As set forth in Section 6, when the bitter tastant, denatonium, was present at a concentration of 5 mM in an in vitro assay, the inhibition identified were active at levels as low as 1 mM, and generally at 5 mM.

Behavioral, physiologic, or biochemical methods may be used to determine whether G-protein activation has occurred. Behavioraland physiologic methods may be practiced in vivo. As an example of a behavioral measurement, the tendency of a test animal to voluntarily ingest a composition comprising the bitter tastant, in the presence or absence of test inhibitor, may be measured. If the bitter tastant activates a G-protein in the animal, the animal may be expected to experience a bitter taste, which would discourage it from ingesting more of the composition. If the animal is given a choice of whether to consume a composition containing bitter tastant only (with activated G-protein) or a composition containing bitter tastant together with a bitterness inhibitor (with lower levels of activated G-protein), it would be expected to prefer to consume the composition containing the bitterness inhibitor. Thus, the relative preference demonstrated by the animal inversely correlates with the activation of G-protein. For an example of such behavioral experiments, see Section 6 infra.

Physiologic methods include nerve response studies, which may be performed using a nerve operably joined to a taste receptor cell containing tissue, in vivo or in vitro. Since exposure to bitter tastant which results in G-protein activation may result in an action potential in taste receptor cells that is then propagated through a peripheral nerve, measuring a nerve response to a bitter tastant is, inter alia, an indirect measurement of G-protein activation. An example of nerve response studies performed using the glossopharyngeal nerve are set forth in Section 6, infra. Recordation of glossopharyngeal nerve responses is also described in Ninomiya, Y., et al., 1977, Am. J. Physiol. (London) 272:R1002–R1006.

In preferred embodiments, the present invention provides for methods for identifying an inhibitor of bitter taste comprising (i) contacting, in vitro, a taste receptor with a solution comprising a G-protein selected from the group consisting of transducin and gustducin, and a bitter tastant, under conditions suitable for activation of the G-protein by the bitter tastant, and measuring the level of G-protein activation; (ii) in a separate experiment, contacting a taste receptor with a solution comprising a G-protein selected from the group consisting of transducin and gustducin, a bitter tastant, and a test inhibitor, and measuring the level of G-protein activation, where the G-protein is the same as that used in part (i), where the conditions are essentially the same as in part (i); and then (iii) comparing the level of activation of the G-protein measured in part (i) with the level of activation of the G-protein measured in part (ii), wherein a lower level of activated G-protein in the presence of the test inhibitor has a positive correlation with an ability of the test inhibitor to inhibit the perception of a bitter taste associated with the tastant.

The taste receptor may be one which has been fully or partially isolated from other molecules, or which may be present as part of a crude or semi-purified extract. As a non-limiting example, the taste receptor may be present in a preparation of taste receptor cell membranes. In particular embodiments of the invention, such taste receptor cell membranes may be prepared as set forth in Ming, D. et al., 1998, Proc. Natl. Sci. U.S.A. 95:8933–8938, incorporated by reference herein. Specifically, bovine circumvallate papillae ("taste tissue", containing taste receptor cells), may be hand dissected, frozen in liquid nitrogen, and stored at −80° C. prior to use. The collected tissues may then be homogenized with a Polytron homogenizer (three cycles of 20 seconds each at 25,000 RPM) in a buffer containing 10 mM Tris at pH 7.5, 10% vol/vol glycerol, 1 mM EDTA, 1 mM DTT, 10 μg/μl pepstatin A, 10 μg/μl leupeptin, 10 μg/μl aprotinin, and 100 μM 4-(2-aminoethyl) benzenesulfoyl fluoride hydrochloride. After particulate removal by centrifugation at 1,500×g for 10 minutes, taste membranes may be collected by centrifugation at 45,000×g for 60 minutes. The pelleted membranes may then be rinsed twice, resuspended in homogenization buffer lacking protease inhibitors, and further homogenized by 20 passages through a 25 gauge needle. Aliquots may then be either flash frozen or stored on ice until use. As another non-limiting example, the taste receptor may be derived from recombinant clones (see Hoon, M. R. et al., 1995, Biochem. J. 309(part 2):629–636.

The gustducin or transducin utilized in the assay may either be molecules present in a taste cell extract or exogenously supplied. In the latter case, gustducin or transducin may be purified from a natural source or may be recombinantly expressed. It should be noted that, in specific non-limiting embodiments, if α-gustducin or α-transducin subunits are used, β and γ units, for example in the form of a combined βγ subunit, should be added to the reaction mixture to enable activation of the heterotrimer; as set forth above, α-gustducin and α-transducin may be combined with βγ subunits from other G proteins. βγ subunits may be prepared from natural sources of may be recombinantly expressed. As a non-limiting example, βγ subunits may be prepared by the method set forth in Fung, B. K., et al., 1981, Proc. Natl. Acad. Sci. U.S.A. 78:152–156 and/or Bubis, J. & Khorana, H. G., 1990, J. Biol. Chem. 265:12995–12999. Alpha and βγ subunits may be combined, for example, as set forth in Ming, D. et al., 1998, Proc. Natl. Sci. U.S.A. 95:8933–8938, such that in vitro translated α-gustducin may be incubated for minutes at room temperature with βγ subunits from bovine retina in 10 mM Tris, pH 8.0/10 mM 3-[(3-cholamidopropyl)dimethylammonio]-1-propanesulfonate (CHAPS).

Taste receptor is contacted with gustducin or transducin and tastant, in the presence or absence of test inhibitor, under conditions suitable for activation of the G-protein present. As a specific, non-limiting example, a taste membrane preparation may be used which comprises taste receptors, having a protein concentration of about 0.25–1 mg/ml, in an incubation buffer which is 25 mM Tris, pH 7.5; 2 mM $MgCl_2$; 5 mM dithiothreitol; 100 mM NaCl; 100 μM GDP; 0.5 μM guanosine 5'-[γ-thio]triphosphate (GTP[γS]). Gustducin (for example, in vitro-translated gustducin) may be added to this mix to a final concentration of 20–200 pM, preferably about 40 pM, or transducin (for example, native transducin) maybe added to a final concentration of 0.2–1.0 μM, preferably about 0.4 μM. In specific non-limiting embodiments, a subunits of transducin or gustducin may be combined with βγ subunits prior to this step, as set forth above. To the reaction mixture comprising taste receptors and gustducin or transducin, test inhibitor and/or bitter tastant may be added, and the resulting solution incubated to permit interaction of the elements. For gustducin-containing mixtures, incubation is preferably performed at refrigeranted temperatures, for example on ice, for between about one and three hours. For transducin, incubation is preferably performed at room temperature or slightly above room temperature, for example, at 30° C., for about one hour.

After the taste receptor, G-protein, test inhibitor and/or bitter tastant have been contacted for an appropriate period of time, activation of G-protein may be determined. In preferred embodiments, activation is assessed by a trypsin digestion assay. It has previously been determined that when the products of such trypsin digestion assays are subjected to SDS-PAGE, inactive gustducin (GDP bound) gives rise to an approximately 23–25 kilodalton band, whereas active gustducin (GTPγS bound) gives rise to an approximately 37 kilodalton band, and inactive transducin (GDP bound) gives rise to a dimer band of approximately 23–25 kilodalton, whereas active transducin (GTPγS bound) gives rise to an approximately 32 kilodalton band. In a specific, non-limiting example, to perform a trypsin digestion assay according to the invention, TPCK-treated trypsin (1:25 trypsin to total protein in the reaction mixture) may be added, and the digestion may be performed at room temperature for about 15 minutes and stopped by adding soybean trypsin inhibitor (6:1 mol/mol inhibitor to trypsin). After the trypsin digestion, samples may be diluted with Laemmli buffer (Laemmli. U. K., 1970, Nature (London) 227:680–685) and separated by SDS/PAGE by using a 4–20% gel and Trisglycine buffer. The separated polypeptides may then be transferred by electro-blotter to a poly (vinylidene difluoride) membrane blocked by the addition of 5% BLOTTO [50 mM Tris-HCl, pH 7.4/100 mM NaCl/5% nonfat dry milk], (30 min). G-protein peptides may then be visualized by binding of antibody directed toward transducin or gustducin, followed, for example, by binding of a detectably labeled secondary antibody. If a horseradish peroxidase-labeled secondary antibody is used, binding may be visualized by developing with bicinchoninic acid staining reagents and exposure to x-ray film. The presence of a 37 kilodalton band correlates with the presence of activated gustducin, and the presence of a 32 kilodalton band correlates with the presence of activated transducin.

Antibodies directed toward gustducin or transducin may be prepared using methods known in the art. For example, an anti-gustducin antibody may be prepared by inoculating a suitable animal with keyhole limpet hemocyanin conjugated to a peptide comprising amino acids 95 to 109 of rat α-gustducin (Takami, S., et al., 1994, Mol. Brain Res. 22:193–203). Monoclonal antibody TF15 (American Qualex, La Mirada, Calif.) was raised against transducin (Navon, S. E. & Fung, B. K.-K., 1988, J. Biol. Chem. 263:489–496) and was found to cross-react with gustducin. See also Ming, D. et al., 1998, Proc. Natl. Acad. Sci. U.S.A. 95:8933–8938; and Ruiz-Avila, L., et al., 1995, Nature (London) 376:80–85.

Test inhibitors which inhibit activation of G-proteins by bitter tastants, identified by any of the above methods, may then be subjected to further testing to either confirm their inhibitory activity and/or to determine whether they act not only as bitterness inhibitors but also as inhibitor sweeteners. To confirm activity, the results of one of the three classes of methods (behavioral, physiologic, in vitro) set forth above may be confirmed by testing the results using one of the other above-disclosed methods. For example, in vitro results may be confirmed by physiologic and/or behavioral studies.

To determine whether an inhibitor acts as an inhibitor sweetener, the ability of the compound to induce the perception of sweet taste may be evaluated by behavioral, physiologic, or in vitro methods as set forth above. Non-limiting examples of inhibitor sweeteners include saccharin, acesulfame K, Na cyclamate, aspartame, D-tryptophan and D-phenylalanine.

For example, a behavioral study may be performed where a test animal may be offered the choice of consuming a composition comprising the putative inhibitor sweetener, and the same composition without the added compound. A preference for the composition comprising test compound, indicated, for example, by greater consumption, would have a positive correlation with inhibitor sweetener activity. The base composition used for testing preferably does not contain perceptible amounts of a bitter tastant to avoid confusion between bitterness inhibitor and inhibitor sweetener activity.

As the transducin of sweet taste is associated with increases in second messenger molecules, such as cAMP, the ability of a bitterness inhibitor to act as an inhibitor sweetener may be evaluated by measuring changes in second messenger levels associated with exposure to the compound, where an increase in these levels correlates with sweet taste. Such measurements may be made, for example, by quench flow systems known in the art. See Huang, L. et al., 1999, Nature Neurosci. 2:1055–1062.

5.2 Compositions Containing Inhibitors and their Uses

The present invention provides for methods of inhibiting a bitter taste resulting from contacting a taste tissue of a subject with a bitter tastant, comprising administering to the subject an effective amount of a bitterness inhibitor, such as a bitterness inhibitor identified by measuring G-protein activation as set forth in Section 5.1 supra. The present invention also provides for methods of inhibiting a bitter taste of a composition, comprising incorporating, in the composition, an effective amount of a bitterness inhibitor. An "effective amount" of the bitterness inhibitor is an amount that subjectively decreases the perception of bitter taste and/or that is associated with a detectable decrease in G-protein activation as measured by one of the above assays. In specific, non-limiting embodiments of the invention, the bitterness inhibitor may be selected from the group consisting of adenosine 5' monophosphate ("AMP"); thymidine 5' monophosphate, adenosine 5' diphosphate, adenosine 3' monophosphate (3'-AMP), adenosine 5'-succinate, adenosine 5' triphosphate ("ATP"), adenosine 2' monophosphate, 5'-cytidylic acid, and inosinic acid.

The present invention also provides for a method of producing the perception of a sweet taste by a subject, comprising administering, to the subject, a composition comprising a compound that acts as a bitterness inhibitor in addition to eliciting a sweet taste. The composition may comprise an amount of inhibitor sweetener that is effective in producing a taste recognized as sweet by a subject.

Accordingly, the present invention provides for compositions comprising bitterness inhibitors, including bitterness inhibitors which act as inhibitor sweeteners. Such compositions include any substances which may come in contact with taste tissue of a subject, including but not limited to foods, pharmaceuticals, dental products, cosmetics, and wetable glues used for envelopes and stamps.

In one set of embodiments, a bitterness inhibitor is used to counteract the perception of bitterness associated with a co-present bitter tastant. In these embodiments, a composition of the invention comprises a bitter tastant and a bitterness inhibitor, where the bitterness inhibitor is present at a concentration which inhibits bitter taste perception. For example, when the concentration of bitter tastant in the composition and the concentration of bitterness inhibitor in the composition are subjected to an assay as disclosed in Section 5.1 supra, the bitterness inhibitor inhibits the activation of G-protein by the bitter tastant.

Suitable bitterness inhibitors include, but are not limited to, adenosine 5' monophosphate; thymidine 5' monophosphate; adenosine 5' diphosphate; adenosine 3' monophosphate; adenosine 5'-succinate; adenosine 5' triphosphate; adenosine 2' monophosphate; 5'-cytidylic acid; and inosinic acid. The amount of bitterness inhibitor added to a composition comprising a bitter tastant may vary depending on the amount of bitter tastant present, other compounds present in the composition, and the species of animal intended to taste the composition. In specific, non-limiting embodiments of the invention, the bitterness inhibitor may be present at a concentration between about 0.01 and 50 mM.

In specific, non-limiting embodiments, where AMP is used as the bitterness inhibitor, a composition comprising a bitter tastant may further comprise a concentration of AMP of between about 0.01 and 20 mM, preferably between about 1 and 5 mM.

In specific, non-limiting embodiments, where thymidine 5' monophosphate is used as the bitterness inhibitor, a composition comprising a bitter tastant may further comprise a concentration of thymidine 5' monophosphate of between about 0.01 and 20 mM, preferably between about 1 and 5 mM.

In specific, non-limiting embodiments, where adenosine 5' diphosphate is used as the bitterness inhibitor, a composition comprising a bitter tastant may further comprise a concentration of adenosine 5' diphosphate of between about 0.01 and 20 mM, preferably between about 1 and 5 mM.

In specific, non-limiting embodiments, where adenosine 3' monophosphate is used as the bitterness inhibitor, a composition comprising a bitter tastant may further comprise a concentration of adenosine 3' monophosphate of between about 0.01 and 20 mM, preferably between about 1 and 5 mM.

In specific, non-limiting embodiments, where adenosine 5' succinate is used as the bitterness inhibitor, a composition comprising a bitter tastant may further comprise a concentration of adenosine 5' succinate of between about 0.01 and 20 mM, preferably between about 1 and 5 mM.

In specific, non-limiting embodiments, where adenosine 5' triphosphate is used as the bitterness inhibitor, a composition comprising a bitter tastant may further comprise a concentration of adenosine 5' triphosphate of between about 0.01 and 20 mM, preferably between about 1 and 5 mM.

In specific, non-limiting embodiments, where adenosine 2' monophosphate is used as the bitterness inhibitor, a composition comprising a bitter tastant may further comprise a concentration of adenosine 2' monophosphate of between about 0.01 and 20 mM, preferably between about 1 and 5 mM.

In specific, non-limiting embodiments, where 5'-cytidylic acid is used as the bitterness inhibitor, a composition comprising a bitter tastant may further comprise a concentration of 5'-cytidylic acid of between about 0.01 and 20 mM, preferably between about 1 and 5 mM.

In specific, non-limiting embodiments, where inosinic acid is used as the bitterness inhibitor, a composition comprising a bitter tastant may further comprise a concentration of inosinic acid of between about 0.01 and 20 mM, preferably between about 1 and 5 mM.

Where a compound of the invention is an inhibitor sweetener, it may be comprised in compositions which either contain, or do not contain, a bitter tastant. If the composition does contain a bitter tastant, the inhibitor sweetener is present at a concentration which decreases or eliminates the transduction of bitter taste associated with the bitter tastant. This concentration, which may depend upon the concentration of bitter tastant, may be determined using the methods set forth in the preceding section, whereby the amount of inhibitor sweetener required to inhibit G-protein activation may be determined. Preferably, but not by way of limitation, the amount of the inhibitor sweetener present results in the perception of a sweet taste in the subject ingesting the composition.

If the composition does not comprise a bitter tastant, the concentration of inhibitor sweetener may be any concentration that results in the perception of a sweet taste. This amount may be determined by subjective and/or psychophysical methods (e.g., taste tests in focus groups), or by behavioral studies such as those described above. In specific non-limiting embodiments, the concentration of inhibitor sweetener present may be between about 0.001–20 mM.

The present invention may be used to improve the taste of foods by decreasing or eliminating the aversive effects of bitter tastants. Where the inhibitors are inhibitor sweeteners, they may be used to improve food flavor by producing a sweet taste. If a bitter tastant is a food preservative, the inhibitors of the invention may permit or facilitate its incorporation into foods, thereby improving food safety. For foods administered as nutritional supplements, the incorporation of inhibitors of the invention may encourage ingestion, thereby enhancing the effectiveness of these compositions in providing nutrition or calories to a subject.

The inhibitors of the invention may be incorporated into medical and/or dental compositions. Certain compositions used in diagnostic procedures have an unpleasant taste, such as contrast materials and local oral anesthetics. The inhibitors of the invention may be used to improve the comfort of subjects undergoing such procedures by improving the taste of compositions. In addition, the inhibitors of the invention may be incorporated into pharmaceutical compositions, including tablets and liquids, to improve their flavor and improve patient compliance (particularly where the patient is a child or a non-human animal).

The inhibitors of the invention may be comprised in cosmetics to improve their taste features. For example, but not by way of limitation, the inhibitors of the invention may be incorporated into face creams and lipsticks.

In addition, the inhibitors of the invention may be incorporated into compositions that are not traditional foods, pharmaceuticals, or cosmetics, but which may contact taste membranes. Examples include, but are not limited to, soaps, shampoos, toothpaste, denture adhesive, glue on the surfaces of stamps and envelopes, and toxic compositions used in pest control (e.g., rat or cockroach poison).

5.3 Identifying Bitter Tastants

The methods set forth in Section 5.1 may be used to identify and/or characterize bitter tastants. Obtaining such information could not only be used to identify new bitter tastants, but also to better predict how a tastant will be perceived and how it could be modulated. To identify/characterize a bitter tastant, a known bitterness inhibitor is used in the methods described in Section 5.1, and the test substance becomes the putative bitter tastant. The ability of a test tastant to activate a G-protein such as gustducin or transducin and for that activation to be inhibited by a bitterness inhibitor indicates that the tastant is perceived as bitter and has transduction mechanisms similar to the known bitter tastants, such as denatonium and quinine.

6. EXAMPLE

Blocking Taste Receptor Activation of Gustducin Inhibits Gustatory Responses to Bitter Compounds

6.1 Materials and Methods

G Protein Activation Assays. Bovine (Bos primigenius) tongues were collected fresh from a local slaughterhouse and transported on ice to the laboratory. Circumvallate papillae were hand dissected, frozen in liquid nitrogen, and stored at −80° C. until use. The collected taste tissues were homogenized, particulates removed by centrifugation, and enriched taste cell membranes collected as described (Ming, D., et al., 1998, Proc. Natl. Acad. Sci. U.S.A. 95:8933–8938). The pelleted membranes were rinsed twice, resuspended in homogenization buffer lacking protease inhibitors, and further homogenized by 20 passages through a 25-gauge needle. Aliquots were either flash frozen or stored on ice until use. The concentration of protein in the membrane preparations was determined by the Peterson modification of the micro-Lowry method (Peterson, G. L., 1977, Anal. Biochem. 83:346–356). Activation of transducin was based on the published trypsin sensitivity procedure (Ming, D., et al., 1998, Proc. Natl. Acad. Sci. U.S.A. 95:8933–8938, Neer, E. J., et al., 1994, Methods Enzymol. 237:226–239). After the trypsin digestion, samples were diluted with Laemmli buffer (Laemmli. U. K., 1970, Nature (London) 227:680–685) and separated by SDS/PAGE by using a 4–20% gel and Tris-glycine buffer. The separated polypeptides were transferred by electro-blotter to a poly (vinylidene difluoride) membrane, which was blocked by the addition of 5% BLOTTO [50 mM Tris-HCl, pH 7.4/100 mM NaCl/5% nonfat dry milk], (30 min), then transducin peptides were visualized by binding of transducin antiserum and horseradish peroxidase-labeled goat anti-rabbit secondary antibody, followed by developing with bicinchoninic acid staining reagents from Bio-Rad and exposure to x-ray film.

Chemicals. All bitter tastant and buffer chemicals were of the highest purity available and were purchased either from Sigma or Boehringer Mannheim, unless otherwise noted. Rhodopsin was purified in the light as 6 M urea-washed bovine rod outer segments by using published procedures (Mazzoni, M. R, et al., 1991, J. Biol. Chem. 266:14072–14081). Bovine transducin heterotrimer was purified by standard procedures (Fung, B. K.-K., et al., 1981, Proc. Natl. Acad. Sci. U.S.A. 78:152–156). The rabbit polyclonal antitransducin antibody was a kind gift of Mel Simon and John Watson (California Institute of Technology, Pasadena, Calif.).

Behavioral Assays. Multiple sets of male C57BL/6J mice from the Jackson Laboratory were tested. Each set (n=10) was tested with tastant±AMP or GMP. Between tests, mice were provided with acidified water (pH 4.5) for about 2 wk. Tested mice ranged in age from 8 to 20 wk. Mice were individually housed, provided with food ad libitum (Pico Lab Mouse Diet 20 no. 5058; PMI Feeds, St. Louis, Mo.) and presented with distilled water in two sipper bottles for 48 h before testing. During each 48-h test period, a given concentration of tastant was provided in one sipper bottle, whereas the other had distilled water. After 24 h, volumes consumed were recorded, the bottles refilled, and positions reversed (to control for positional cues). Tastants were presented in ascending concentration. Preference ratios were calculated as the fraction of tastant consumed as a percentage of the total volume of liquid consumed. Mean preference ratios and Student's t tests were calculated from total collected data.

Nerve Recording. Glossopharyngeal nerve responses were recorded from male C57BL/6J mice as previously described (Ninomiya, Y., et al., 1997, Am. J. Physiol. (London) 272:R1002–RI006). Each mouse was anesthetized with intraperitoneal injection of sodium pentobarbital (40–50 mg/kg) and maintained at a surgical level of anesthesis with supplemental injections of the drug. The trachea was cannulated, and the mouse was then fixed in the supine position with a head holder to allow dissection of the glossopharyngeal nerve. The hypoglossal nerve was transected bilaterally to prevent inadvertent tongue movements. The right glossopharyngeal nerve was exposed by removal of the digastric muscle and posterior horn of the hyoid bone. The glossopharyngeal nerve was then dissected free from underlying tissues and cut near its entrance to the posterior foramen lacerum. The entire nerve was placed on a silver wire electrode for whole nerve recording. An indifferent electrode was positioned nearby in the wound. Neural responses resulting from topical application of tastants to the tongue were fed into an amplifier and displayed on an oscilloscope screen. Whole nerve responses were integrated by using an RMS-DC converter (Hendrick, Tallahassee, Fla.) with a time constant of 0.5 s. For chemical stimulation of the circumvallate and foliate papillae, an incision was made on each side of the animal's face from the comer of the mouth to just above the angle of the jaw, the papillae were exposed, and their trenches opened via slight tension applied through a small suture sewn in the tip of the tongue. Tastant solutions were delivered to the tongue by gravity flow, and flowed over the tongue for a controlled period. The stability of each preparation was monitored by the periodic application of 0.1 M $NH_4Cl$. A recording was considered to be stable when the 0.1 M $NH_4Cl$ response magnitudes at the beginning and end of each stimulation series deviated by no more than 15%. Only responses from stable recordings were used in the data analysis. In the analysis of whole nerve responses, the magnitudes of the integrated response at 20, 25, 30, 35. and 40 s after stimulus onset were measured and averaged to generate tonic responses: the tonic response represents the sustained nerve response to continuous tastant stimulation of taste receptor cells. The relative tonic response for each stimulus was obtained by normalization to the response from 0.1 M $NH_4Cl$ (the tonic response of $NH_4Cl$ was defined as 1.0). Student's t test was used for statistical analysis.

6.2 Results

Figure 1B:
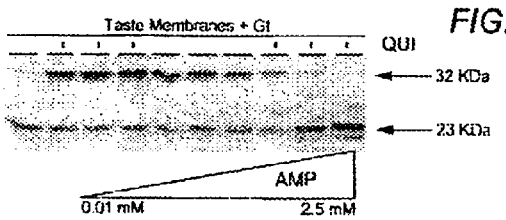
Figure 1C:
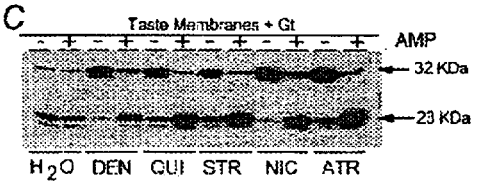
Figure 1D:
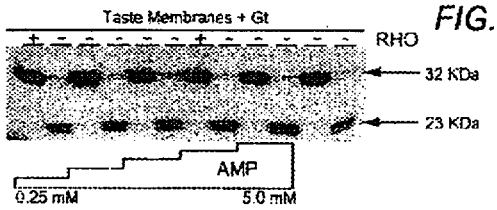
Figure 1E:
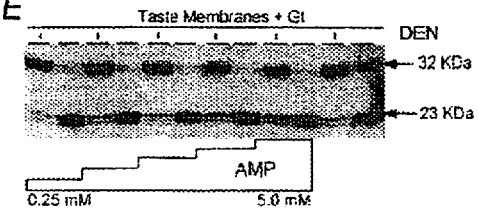

The active (GTP-bound) form of G proteins such as gustducin and transducin can be distinguished from the inactive (GDP-bound) form by limited trypsin digestion (Fung, B. K.-K. & Nash, C. R., 1983, J. Biol. Chem. 258:10503–10510; Halliday, K. R., et al., 1984, J. Biol. Chem. 259:516–525). Using transducin as a reporter in this in vitro assay, we identified compounds that inhibited gustatory responses to bitter compounds. Taste membrane activation of transducin by the bitter compounds denatonium benzoate (DEN) and quinine hydrochloride (QUI) was inhibited in a dose-dependent fashion by AMP (FIGS. 1A and 1B). The inhibitory effect of AMP generalized to every bitter compound that activated transducin in the presence of taste membranes: DEN, QUI, strychnine, nicotine, atropine (FIG. 1C), sparteine, naringin, caffeic acid, and quinacrine. The inhibitory effect of AMP was specific and required taste receptors, because AMP did not inhibit rhodopsin-mediated activation of transducin (FIG. 1D). GMP did not inhibit taste membrane activation of transducin in response to DEN (FIG. 1E) or other bitter tastants. suggesting specificity of binding. Several AMP-related compounds potently inhibited DEN/taste receptor activation of transducin: thymidine 5'-monophosphate, ADP, 3'AMP, adenosinc 5'-succinate, ATP (FIG. 2) and adenosine 2'-monophosphate. 5'-Cytidylic acid, and inosinic acid partially inhibited DEN/taste membrane activation of transducin (FIG. 2). As with GMP (FIG. 1E), adenosine 5'-carboxylate, adenosine 5'-monosulfate, theophylline, adenine, adenosine, cAMP and caffeine did not block activation of transducin by DEN-stimulated taste membranes (FIG. 2).

Figure 3A:
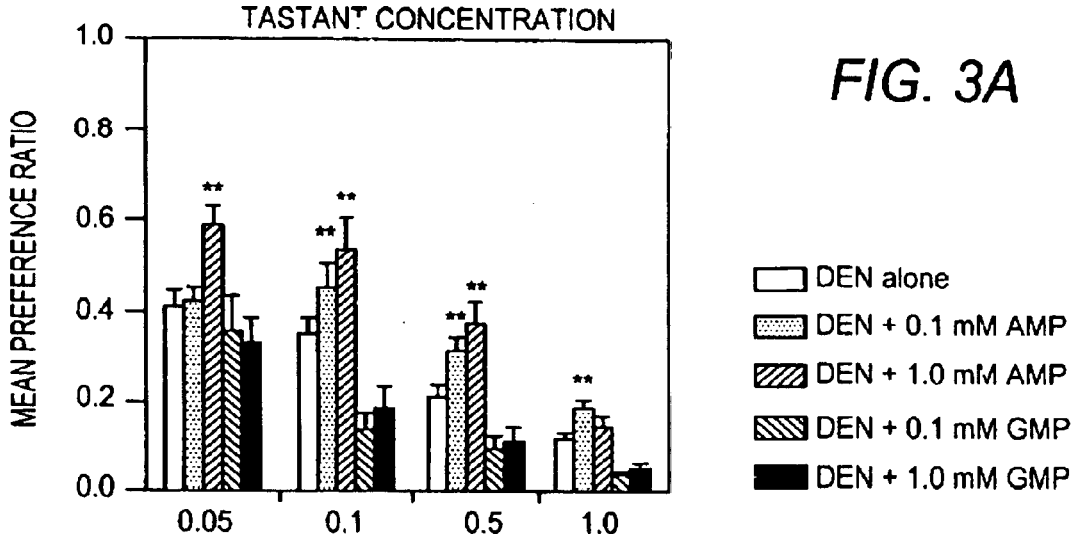
Figure 3B:
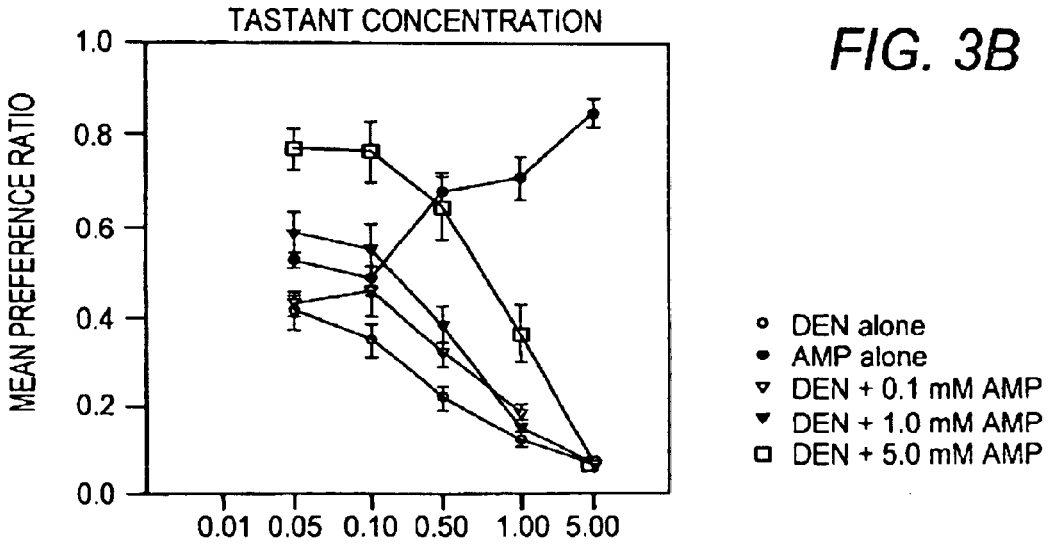
Figure 3C:
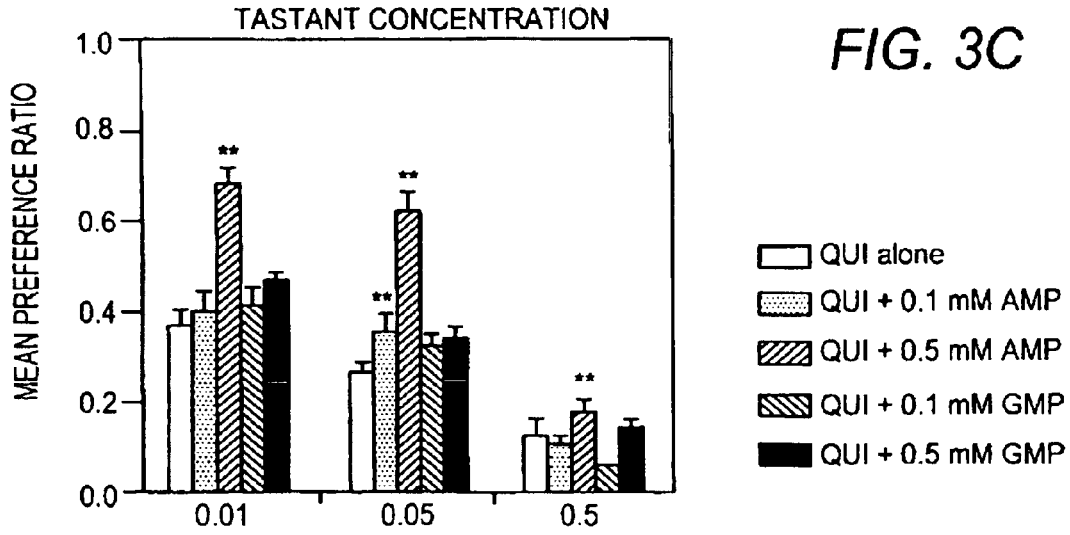
Figure 3D:
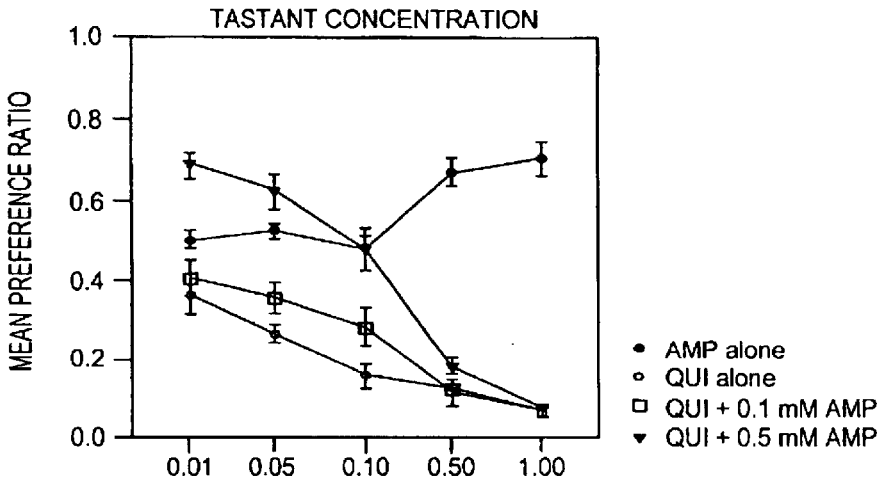
Figure 3E:
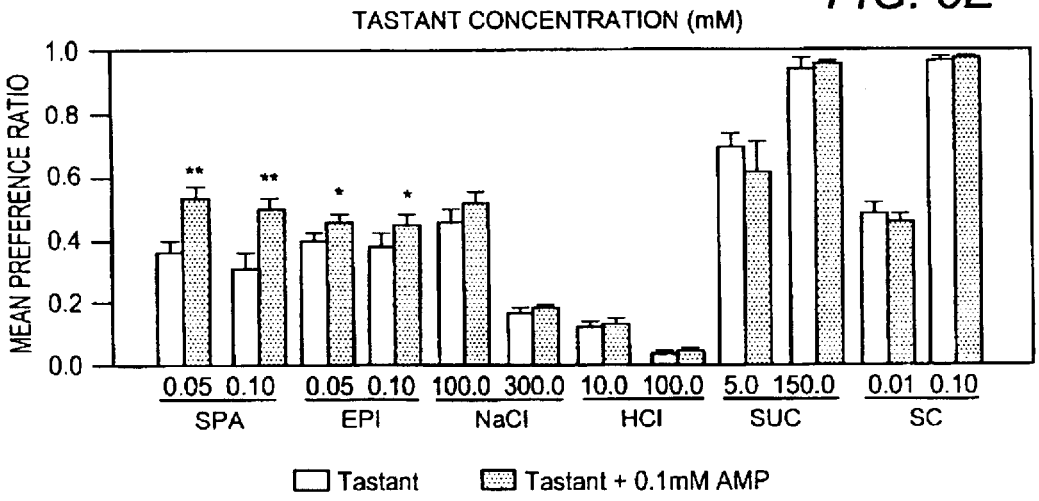

To determine whether AMP, as distinct from GMP, would diminish the gustatory responses to bitter compounds, two-bottle preference tests (Harder, D. B., et al., 1989, Chem. Senses 14:547–564) were carried out on mice presented with various tastants±AMP or GMP. AMP, but not GMP, inhibited the aversive responses of mice to DEN (FIGS. 3A and 3B) and QUI (FIGS. 3C and 3D). The inhibitory effect of AMP gradually decreased as the concentration of bitter tastant increased and was eliminated at the highest concentrations of DEN and QUI tested (5.0 and 1.0 mM. respectively) (FIGS. 3A–D). Several other tastants that humans characterize as bitter [sparteine and (−)-epicatechin (Glendinning, J. 1., 1994, Physiol. Behav. 56:1217–1227)], sweet [sucrose and the high-potency artificial sweetener SC45647 (Nofre, C., et al., inventors, Université Claude Bernard, Lyon 1, France, assignee, "Sweetening Agents", U.S. Pat. No. 4,921,939, May 1, 1990)], sour (HCl), or salty (NaCl) were also tested±AMP. AMP inhibited the aversive responses to the two bitter compounds, sparteine and epicatechin, but did not affect the behavioral responses to sucrose, SC45647, NaCl, or HCl (FIG. 3E).

Figure 4A:
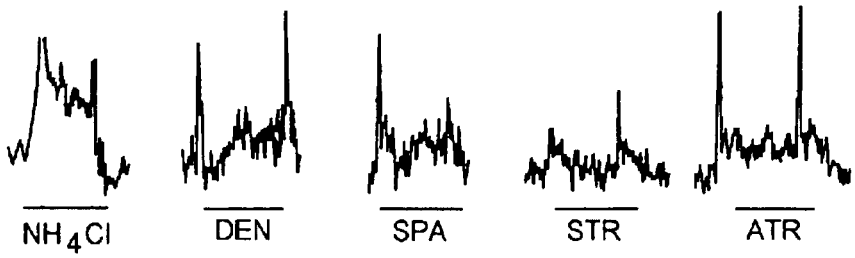
Figure 4B:
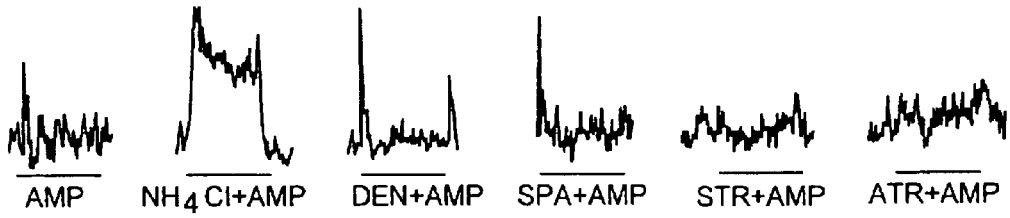
Figure 4C:
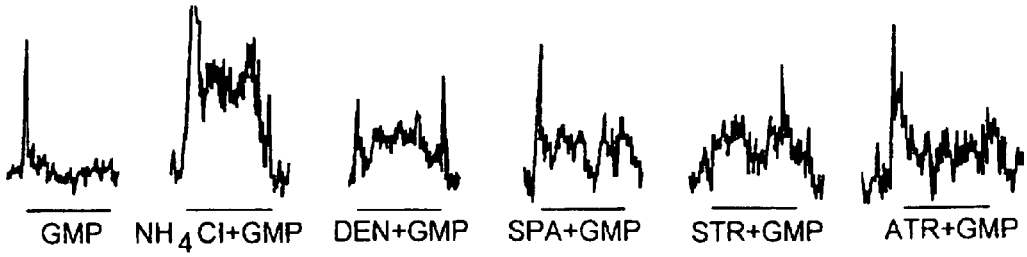
Figure 4D:
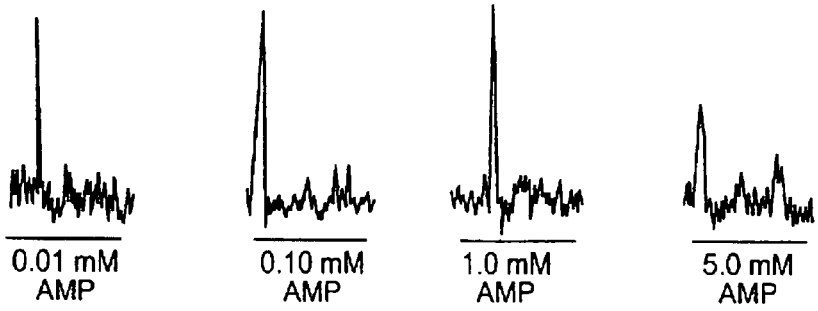
Figure 4E:
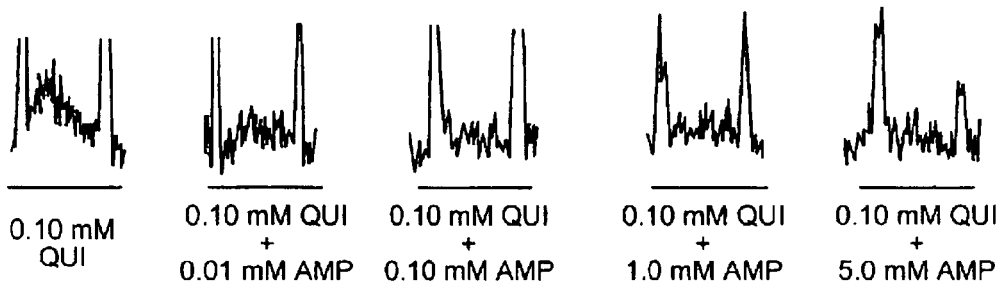
Figure 4F:
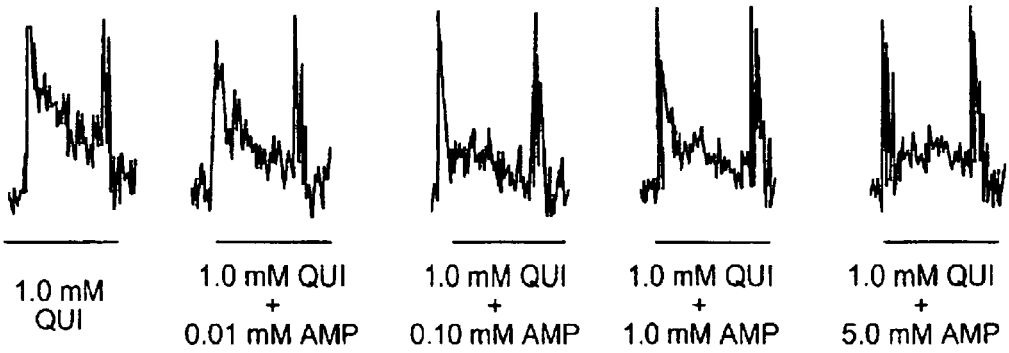
Figure 4G:
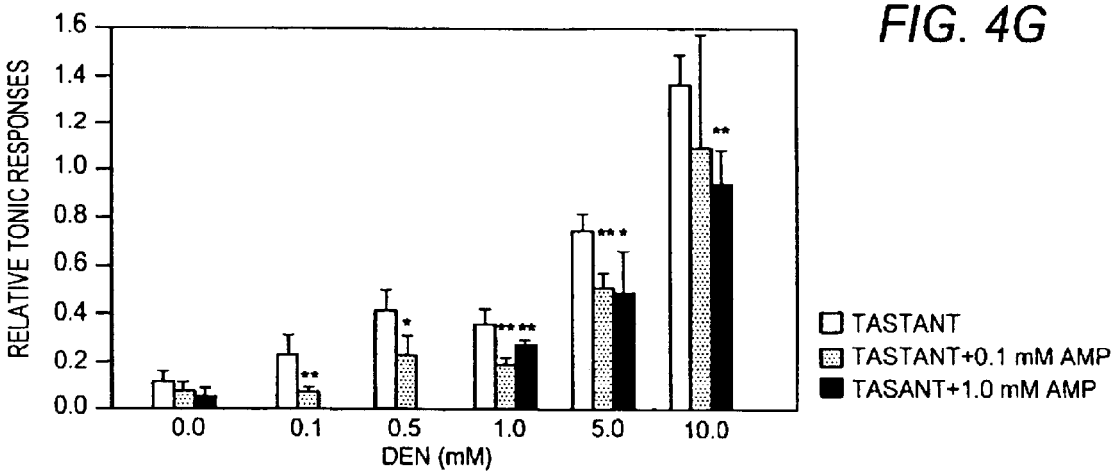
Figure 4H:
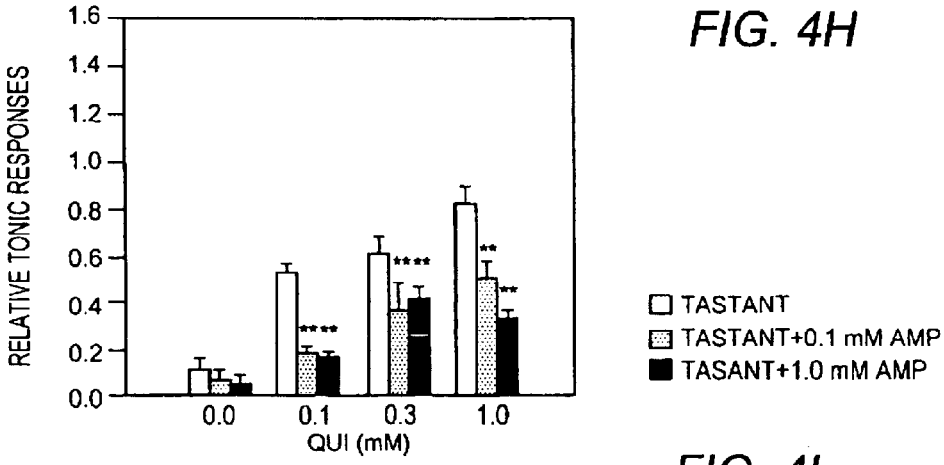
Figure 4I:
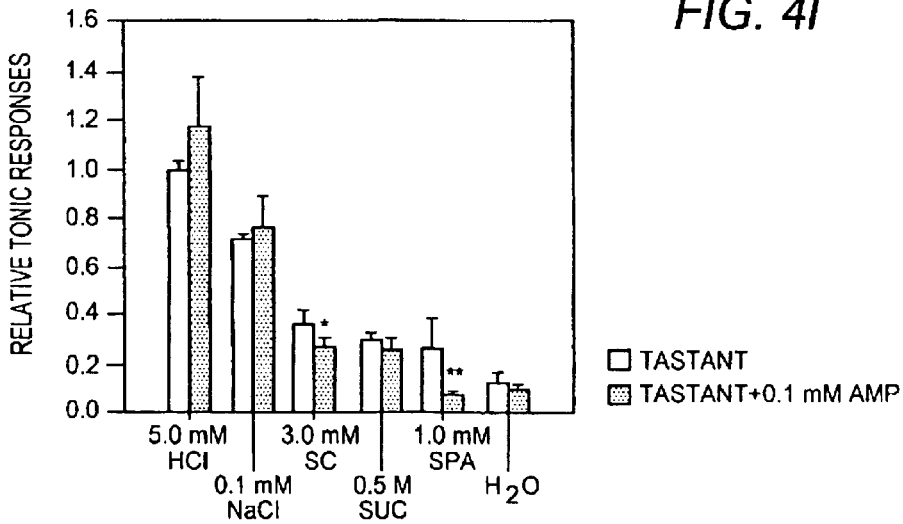

To determine whether the inhibition of aversive responses to bitter compounds by AMP was because of peripheral taste inhibition (as predicted by the biochemical data of FIGS. 1 and 2) we recorded summated glossopharyngeal nerve responses of mice (Ninomiya, Y., et al., 1997, Am. J. Physiol. (London) 272:R1002–RI006) to various tastants±AMP or GMP. The glossopharyngeal nerve innervates taste receptor cells of the posterior tongue and in mice is responsive to salty, sweet, sour, and bitter stimuli (Ninomiya, Y., et al. 1984, Brain Res. 302:305–314). AMP (0.1 mM) significantly inhibited the nerve responses to DEN, QUI, sparteine, strychnine, and atropine (FIGS. 4A–F). GMP (0.1 mM) had no effect on the glossopharyngeal responses to any of these bitter compounds (FIG. 4C). The glossopharyngeal responses increased as QUI or DEN concentrations were raised: AMP (0.1 and 1.0 mM) significantly inhibited these nerve responses (FIGS. 4D–H). In contrast, AMP did not affect the nerve responses to $NH_4Cl$, HCl, NaCl, or sucrose (FIG. 4I), consistent with the behavioral responses. Interestingly, although AMP inhibited slightly the glossopharyngeal responses to the artificial sweetener SC45647 (FIG. 4I), it did not diminish the behavioral responses to this compound (FIG. 3E).

6.3 Discussion

AMP and closely related compounds inhibited in vitro activation of transducin by taste membranes plus DEN, QUI, and several other bitter compounds. This effect was specific to the bitter-responsive heptahelical receptors presumably present in taste membranes and was not caused by nonspecific or general activation of rhodopsin-like receptors. AMP and like compounds also blocked behavioral and gustatory nerve responses to DEN, QUI, and other bitter compounds, but did not affect responses to NaCl, HCl, or sucrose. AMP did diminish glossopharyngeal responses to the high-potency sweetener SC45647, although it did not affect behavioral responses to this inosinic acid all inhibited in vitro taste receptor responses, whereas GMP did not, indicating selectivity in the binding of these compounds. The rapidity of AMP's actions in the electrophysiological assays argues against an intracellular site of action and suggests that AMP is probably acting at a cell-surface receptor. However, the present data do not distinguish between competitive or noncompetitive modes of action of AMP at the receptor.

High concentrations of DEN, QUI, and other bitter tastants overcame AMP's inhibition of aversive responses, suggesting either than AMP is acting as a competitive inhibitor or that the bitter tastants activated other AMP-resistant bitter transduction pathways in addition to gustducin/transducin—mediated pathways, consistent with residual responsiveness to bitter compounds in gustducin knockout and transgenic mice expressing a mutated form of gustducin that disrupts signal transduction (Wong. G. T., et al., 1996, Nature (London) 381:796–800; Ming. D., et al., 1998, Proc. Natl. Acad. Sci. U.S.A. 95:8933–8938). The existence of multiple bitter transduction pathways is also supported by the observation that inhibition by AMP of glossopharyngeal responses to increasing concentrations of QUI reached a plateau at which glossopharyngeal responses to QUI could not be reduced further.

In recent studies, it has been determined that certain artificial sweeteners inhibit in vitro activation of taste receptors by DEN, QUI, and other bitter compounds; there sweeteners also inhibited behavioral and gustatory nerve responses to these gustducin/transducin coupled bitter compounds. This phenomenon of sweet-bitter "mixture suppression" (Bartoshuk, L. M., 1975, Physiol. Behav. 14:643–649; Formaker. B. K. & Frank, M. E., 1996, Brain Res. 727:79–90) may be explained in part by antagonist binding of sweeteners to the same receptor targets that bind bitter compounds and may relate to previous observations of chemical similarities of high-potency sweeteners and high-potency bitter compounds (Lee. C. K., 1987, Adv. Carbohydr. Chem. Biochem. 45:199–351; Benedetti, E., et al., 1995, J. Pept. Sci. 1:349–359; Shin, W., et al., 1995, J. Med. Chem. 38:4325–4331 21–23). Multiple lines of evidence implicate gustducin/transducin, their coupled receptors, and effector enzymes (e.g., phosphodiesterases and phospholipase C) in bitter transduction (reviewed in Kinnamon, S. C. & Margolskee, R. F., 1996, Curr. Opin. Neurobiol. 6:506–513; Lindemann, B., 1996, Physiol. Rev. 76:719–766). In addition to gustducin and transducin. the G proteins $G_s$ $G_{i3}$, and $G_{14}$ are also present in taste receptor cells (Kinnamon, S. C. & Margolskee, R. F., 1996, Curr. Opin. Neurobiol. 6:506–513; McLaughlin. S. K., et al., 1992, Nature (London) 357:563–569) and may be involved in taste transduction. Biochemical and electrophysiological studies implicate cyclic nucleotides, inositol triphosphate, diacyl glycerol, and $Ca^{2+}$ as second messengers in bitter and/or sweet taste transduction (Tonosaki, K. & Funakoshi, M., 1988, Nature (London) 331:354–356; Behe, P., et al., 1990, J. Gen. Physiol. 96:1061–1084; Bernhardt. S. J., et al., 1996, J. Physiol. (London) 490:325–336; Cummings, T. A., et al., 1996, J. Neurophysiol. 75:1256–1263; Spielman. A. I., et al., 1996, Am. J. Physiol. 270:C926–C931 24–28). Biochemical and genetic data clearly implicate gustducin in the transduction of both bitter and sweet taste qualities: (i) gustducin null mice have markedly diminished behavioral and gustducin nerve responses to both bitter and sweet compounds (Wong. G. T., et al., 1996, Nature (London) 381:796–800); (ii) a mutated form of gustducin disrupted in its interaction with receptors acts as a dominant negative to block both bitter and sweet responsiveness in vivo; (iii) in vitro studies demonstrate that bovine taste receptor-containing membranes and solubilized taste receptors activate gustducin/transducin in the presence of DEN, QUI and several other bitter compounds (Ming. D., et al., 1998, Proc. Natl. Acad. Sci. U.S.A. 95:8933–8938); (iv) although sweet compounds do not activate gustducin/transducin in this assay, our data demonstrate that certain sweeteners block in vitro activation of gustducin/transducin and thereby lead to sweet-bitter "mixture suppression."

Although biochemical and genetic studies of taste G proteins have provided new insights into the molecular nature of the sweet and bitter transduction cascades, physical studies of the taste receptors involved in bitter and sweet transduction (Cagan, R. H. & Morris, R. W., 1979, Proc. Natl. Acad. Sci. U.S.A. 76:1692–1696; Shimazaki. K., et al., 1986, Biochim. Biophys. Acta 884:291–298) have been of limited utility because of the scarcity of material and the lack of high-affinity ligands. Typical naturally occurring bitter and sweet tastants are active in the range of 10–500 mM, whereas the most potent sweet or bitter tastants have thresholds for detection of 10–100 nM. The likelihood of receptor families and multiple independent pathways further compounds the difficulties of characterizing taste receptors. Structure-activity relationship analyses of high-potency sweeteners have led to working models of the physical nature of the receptor's binding pocket (reviewed in Roy. G., 1992, Crit. Rev Food Sci. Nutr. 31:59–77; Schiffman S. S. & Gatlin. C. A., 1993, Neurosci. Biobehav. Rev. 17:313–345); however, these approaches are severely limited by the possibility of receptor heterogeneity and multiple independent pathways for sweetener function. The approach we have presented may have utility for identifying specific subtypes of bitter receptors and naturally occurring and synthetic compounds that act as selective blockers of bitter taste.

Various publications are cited herein which are hereby incorporated by reference in their entireties.

What is claimed is:

1. A method for identifying an inhibitor of bitter taste comprising (i) contacting a taste receptor with a G-protein selected from the group consisting of transducin and gustducin, and a bitter tastant, under conditions suitable for activation of the G-protein by the bitter tastant, and measuring the level of G-protein activation; (ii) in a separate experiment, contacting a taste receptor with a G-protein selected from the group consisting of transducin and gustducin, the bitter tastant, and a test inhibitor under conditions suitable for activation of the G-protein by the bitter tastant, and measuring the level of G-protein activation, where the G-protein is the same as that used in part (i), and where the test inhibitor is adenosine monophosphate or a structural homolog of adenosine monophosphate; and then (iii) comparing the level of activation of the G-protein measured in part (i) with the level of activation of the G-protein measured in part (ii), wherein a lower level of activated G-protein in the presence of the test inhibitor has a positive correlation with an ability of the test inhibitor to inhibit the perception of a bitter taste associated with the tastant.

2. The method of claim 1, where the taste receptor is comprised in an extract of taste receptor cells.

3. The method of claim 2, where the extract is a composition comprising taste cell membranes.

4. The method of claim 2, where the levels of G-protein activation in parts (i) and (ii) are measured by determining the sensitivity of the G-protein to trypsin digestion.

5. The method of claim 3, where the levels of G-protein activation in parts (i) and (ii) are measured by determining the sensitivity of the G-protein to trypsin digestion.

6. The method of claim 4, where the sensitivity of the G-protein to trypsin digestion is evaluated by determining the size of G-protein fragments resulting from exposure of the G-protein to trypsin.

7. The method of claim 5, where the sensitivity of the G-protein to trypsin digestion is evaluated by determining the size of G-protein fragments resulting from exposure of the G-protein to trypsin.

8. The method of claim 1, where the taste receptor is comprised in a taste receptor cell in an animal.

9. The method of claim 8, where the activation of G-protein is measured by nerve recording, wherein an increase in nerve response correlates with G-protein activation.

10. The method of claim 8, where the activation of G-protein is measured by the consumption of a composition comprising the bitter tastant, and wherein an aversive response to the composition has a positive correlation with G-protein activation.

11. The method of claim 1, wherein step (iii) identifies a lower level of activated G-protein in the presence of the test inhibitor, and the test inhibitor is further determined to elicit the perception of sweet taste.

12. A method for identifying an inhibitor of bitter taste comprising (i) contacting, in vitro, a taste receptor with a solution comprising a G-protein selected from the group consisting of transducin and gustducin, and a bitter tastant, under conditions suitable for activation of the G-protein by the bitter tastant, and measuring the level of G-protein activation; (ii) in a separate experiment, contacting a taste receptor with a solution comprising a G-protein selected from the group consisting of transducin and gustducin, the bitter tastant, and a test inhibitor, and measuring the level of G-protein activation, where the G-protein is the same as that used in part (i), and where the test inhibitor is adenosine monophosphate or a structural homolog of adenosine monophosphate; and then (iii) comparing the level of activation of the G-protein measured in part (i) with the level of activation of the G-protein measured in part (ii), wherein a lower level of activated G-protein in the presence of the test inhibitor has a positive correlation with an ability of the test inhibitor to inhibit the perception of a bitter taste associated with the tastant.

13. The method of claim 12, where the taste receptor is comprised in an extract of taste receptor cells.

14. The method of claim 13, where the extract is a composition comprising taste cell membranes.

15. The method of claim 13, where the levels of G-protein activation in parts (i) and (ii) are measured by determining the sensitivity of the G-protein to trypsin digestion.

16. The method of claim 14, where the levels of G-protein activation in parts (i) and (ii) are measured by determining the sensitivity of the G-protein to trypsin digestion.

17. The method of claim 15, where the sensitivity of the G-protein to trypsin digestion is evaluated by determining the size of G-protein fragments resulting from exposure of the G-protein to trypsin.

18. The method of claim 16, where the sensitivity of the G-protein to trypsin digestion is evaluated by determining the size of G-protein fragments resulting from exposure of the G-protein to trypsin.

19. A method for identifying an inhibitor of bitter taste in vivo comprising (i) contacting a taste receptor with a G-protein, selected from the group consisting of transducin and gustducin, and a bitter tastant, under conditions suitable for activation of the G-protein by the bitter tastant, and measuring the level of G-protein activation; (ii) in a separate experiment, contacting a taste receptor with a G-protein selected from the group consisting of transducin and gustducin, the bitter tastant, and a test inhibitor, and measuring the level of G-protein activation, where the G-protein is the same as that used in part (i), and where the test inhibitor is adenosine monophosphate or a structural homolog of adenosine monophosphate; and then (iii) comparing the level of activation of the G-protein measured in part (i) with the level of activation of the G-protein measured in part (ii), wherein a lower level of activated G-protein in the presence of the test inhibitor has a positive correlation with an ability of the test inhibitor to inhibit the perception of a bitter taste associated with the tastant.

20. The method of claim 19, wherein identifying said inhibitors of bitter taste in vivo [comprising] *comprises* (i) offering a test animal the choice of consuming either (a) a composition comprising a bitter tastant or (b) the composition comprising the bitter tastant as well as said [bitter taste] *test* inhibitor; and (ii) comparing the amount of consumption of the composition according to (a) or (b), wherein greater consumption of the composition according to (b) has a positive correlation with an ability of said [bitter taste] *test* inhibitor to inhibit the perception of bitter taste associated with the tastant.

21. The method of claim 19, where said [bitter taste] *test* inhibitor [was] *is* found to inhibit activation of a G-protein by the bitter tastant.

22. The method of claim 20, where said [bitter taste] *test* inhibitor elicits the perception of a sweet taste.

23. A method of inhibiting a bitter taste resulting from contacting a taste tissue of a subject with a bitter tastant, comprising administering to the subject *a composition comprising* an effective amount of a bitterness inhibitor, wherein said bitterness inhibitor is adenosine monophosphate or a structural homolog of adenosine monophosphate*, and wherein the composition comprises at least 0.1 mM of the bitterness inhibitor*.

24. The method of claim 23, wherein the bitterness inhibitor is adenosine 5' monophosphate.

25. The method of claim 23, wherein the bitterness inhibitor is thymidine 5' monophosphate.

26. The method of claim 23, wherein the bitterness inhibitor is adenosine 5' diphosphate.

27. The method of claim 23, wherein the bitterness inhibitor is adenosine 3' monophosphate.

28. The method of claim 23, wherein the bitterness inhibitor is adenosine 5'-succinate.

29. The method of claim 23, wherein the bitterness inhibitor is adenosine 5' triphosphate.

30. The method of claim 23, wherein the bitterness inhibitor is adenosine 2' monophosphate.

31. The method of claim 23, wherein the bitterness inhibitor is 5'-cytidylic acid.

32. The method of claim 23, wherein the bitterness inhibitor is inosinic acid.

33. A method of inhibiting [s] *the* bitter taste of a composition, comprising incorporating, in the composition, an effective amount of a bitterness inhibitor, wherein said bitterness inhibitor is adenosine monophosphate or a structural homolog of adenosine monophosphate*, and wherein the composition comprises at least 0.1 mM of the bitterness inhibitor*.

34. The method of claim 33, wherein the bitterness inhibitor is adenosine 5' monophosphate.

35. The method of claim 33, wherein the bitterness inhibitor is thymidine 5' monophosphate.

36. The method of claim 33, wherein the bitterness inhibitor is adenosine 5' diphosphate.

37. The method of claim 33, wherein the bitterness inhibitor is adenosine 3' monophosphate.

38. The method of claim 33, wherein the bitterness inhibitor is adenosine 5'-succinate.

39. The method of claim 33, wherein the bitterness inhibitor is adenosine 5' triphosphate.

40. The method of claim 33, wherein the bitterness inhibitor is adenosine 2' monophosphate.

41. The method of claim 33, wherein the bitterness inhibitor is 5'-cytidylic acid.

42. The method of claim 33, wherein the bitterness inhibitor is inosinic acid.

[43. The method of claim 11, further comprising administering to the subject, a composition comprising said bitterness inhibitor that acts as a bitterness inhibitor in addition to eliciting a sweet taste.]

[44. The composition of claim 43, comprising a bitter tastant and one or more of said bitterness inhibitors is present at a concentration which inhibits bitter taste perception.]

[45. The composition of claim 44, wherein the bitterness inhibitor is adenosine 5' monophosphate.]

[46. The composition of claim 44, wherein the bitterness inhibitor is thymidine 5' monophosphate.]

[47. The composition of claim 44, wherein the bitterness inhibitor is adenosine 5' diphosphate.]

[48. The composition of claim 44, wherein the bitterness inhibitor is adenosine 3' monophosphate.]

[49. The composition of claim 44, wherein the bitterness inhibitor is adenosine 5'-succinate.]

[50. The composition of claim 44, wherein the bitterness inhibitor is adenosine 5' triphosphate.]

[51. The composition of claim 44, wherein the bitterness inhibitor is adenosine 2' monophosphate.]

[52. The composition of claim 44, wherein the bitterness inhibitor is 5'-cytidylic acid.]

[53. The composition of claim 44, wherein the bitterness inhibitor is inosinic acid.]

[54. The composition of claim 43, comprising a bitter tastant and one or more of said bitterness inhibitors, is present at a concentration which inhibits bitter taste perception and which elicits the perception of a sweet taste.]

[55. The composition of claim 43, wherein one or more of said bitterness inhibitor, is present at a concentration which elicits the perception of a sweet taste.]

56. A method for identifying a bitter tastant comprising (i) contacting a taste receptor with a G-protein, selected from the group consisting of transducin and gustducin, and a test-tastant, and measuring the level of G-protein activation; (ii) in a separate experiment, contacting a taste receptor with a G-protein selected from the group consisting of transducin and gustducin, the test tastant, and a bitterness inhibitor, wherein said bitterness inhibitor is adenosine monophosphate or a structural homolog of adenosine monophosphate, and measuring the level of G-protein activation, where the G-protein is the same as that used in part (i), and then (iii) comparing the level of activation of the G-protein measured in part (i) with the level of activation of the G-protein measured in part (ii), wherein a lower level of activated G-protein in the presence of said bitterness inhibitor has a positive correlation with an ability of the test tastant to elicit the perception of a bitter taste.

57. The method of claim 1, wherein the [bitterness] *test* inhibitor is adenosine 5' monophosphate.

58. The method of claim 1, wherein the [bitterness] *test* inhibitor is thymidine 5' monophosphate.

59. The method of claim 1, wherein the [bitterness] *test* inhibitor is adenosine 5' diphosphate.

60. The method of claim 1, wherein the [bitterness] *test* inhibitor is adenosine 3' monophosphate.

61. The method of claim 1, wherein the [bitterness] *test* inhibitor is adenosine 5'-succinate.

62. The method of claim 1, wherein the [bitterness] *test* inhibitor is adenosine 5'-triphosphate.

63. The method of claim 1, wherein the [bitterness] *test* inhibitor is adenosine 2'-monophosphate.

64. The method of claim 1, wherein the [bitterness] *test* inhibitor is 5'-cytidylic acid.

65. The method of claim 1, wherein the [bitterness] *test* inhibitor is inosinic acid.

*66. The method of claim 23, wherein said bitterness inhibitor elicits a sweet taste.*

*67. The method of claim 66, wherein the bitter tastant and the bitterness inhibitor are each present at a concentration such that the composition inhibits bitter taste perception.*

*68. The method of claim 67, wherein the bitterness inhibitor is adenosine 5' monophosphate.*

*69. The method of claim 67, wherein the bitterness inhibitor is thymidine 5' monophosphate.*

*70. The method of claim 67, wherein the bitterness inhibitor is adenosine 5' diphosphate.*

*71. The method of claim 67, wherein the bitterness inhibitor is adenosine 3' monophosphate.*

*72. The method of claim 67, wherein the bitterness inhibitor is adenosine 5'-succinate.*

*73. The method of claim 67, wherein the bitterness inhibitor is adenosine 5' triphosphate.*

*74. The method of claim 67, wherein the bitterness inhibitor is adenosine 2' monophosphate.*

*75. The method of claim 67, wherein the bitterness inhibitor is 5'-cytidylic acid.*

*76. The method of claim 67, wherein the bitterness inhibitor is inosinic acid.*

*77. The method of claim 66, wherein the bitter tastant and the bitterness inhibitor are each present at a concentration such that the composition inhibits bitter taste perception and elicits the perception of a sweet taste.*

*78. The method of claim 66, wherein the bitterness inhibitor is present at a concentration which elicits the perception of a sweet taste.*

*79. The method of claim 23, wherein the bitterness inhibitor and the bitter tastant are co-administered.*

*80. The method of claim 23, wherein the bitter tastant is a food.*

*81. The method of claim 23, wherein the bitter tastant is a pharmaceutical.*

*82. The method of claim 23, wherein the bitter tastant is a cosmetic.*

*83. The method of claim 23, wherein the bitter tastant is a soap.*

*84. The method of claim 23, wherein the bitter tastant is a shampoo.*

*85. The method of claim 23, wherein the bitter tastant is a denture adhesive.*

*86. The method of claim 23, wherein the bitter tastant is a glue.*

*87. The method of claim 23, wherein the bitter tastant is a toxic composition used in pest control.*

*88. The method of claim 23, wherein the bitter tastant comprises at least 1 mM of the bitterness inhibitor.*

*89. The method of claim 23, wherein the bitter tastant comprises between about 1 and about 20 mM of adenosine 5' monophosphate.*

*90. The method of claim 23, wherein the bitter tastant comprises between about 1 and about 5 mM of adenosine 5' monophosphate.*

*91. The method of claim 23, wherein the bitterness inhibitor sweetens the bitter tastant.*

*92. The method of claim 23, wherein the subject is a human.*

*93. The method of claim 92, wherein the subject is a child.*

*94. The method of claim 23, wherein the subject is an animal.*

*95. The method of claim 94, wherein the subject is livestock.*

*96. The method of claim 33, wherein the composition is a food.*

*97. The method of claim 33, wherein the composition is a pharmaceutical.*

*98. The method of claim 33, wherein the composition is a cosmetic.*

*99. The method of claim 33, wherein the composition is a soap.*

*100. The method of claim 33, wherein the composition is a shampoo.*

*101. The method of claim 33, wherein the composition is a denture adhesive.*

*102. The method of claim 33, wherein the composition is a glue.*

*103. The method of claim 33, wherein the composition is a toxic composition used in pest control.*

*104. The method of claim 33, wherein the composition comprises at least 1 mM of the bitterness inhibitor.*

*105. The method of claim 33, wherein the composition comprises between about 1 and about 20 mM of adenosine 5' monophosphate.*

*106. The method of claim 33, wherein the composition comprises between about 1 and about 5 mM of adenosine 5' monophosphate.*

*107. The method of claim 33, wherein the bitterness inhibitor sweetens the composition.*

*108. The method of claim 56, wherein the bitterness inhibitor is adenosine 5' monophosphate.*

*109. The method of claim 56, wherein the bitterness inhibitor is thymidine 5' monophosphate.*

*110. The method of claim 56, wherein the bitterness inhibitor is adenosine 5' diphosphate.*

*111. The method of claim 56, wherein the bitterness inhibitor is adenosine 3' monophosphate.*

*112. The method of claim 56, wherein the bitterness inhibitor is adenosine 5'-succinate.*

*113. The method of claim 56, wherein the bitterness inhibitor is adenosine 5'-triphosphate.*

*114. The method of claim 56, wherein the bitterness inhibitor is adenosine 2'-monophosphate.*

*115. The method of claim 56, wherein the bitterness inhibitor is 5'-cytidylic acid.*

*116. The method of claim 56, wherein the bitterness inhibitor is inosinic acid.*

* * * * *

UNITED STATES PATENT AND TRADEMARK OFFICE

CERTIFICATE OF CORRECTION

PATENT NO. : RE 40,594 E
APPLICATION NO. : 11/391670
DATED : December 2, 2008
INVENTOR(S) : Margolskee et al.

It is certified that error appears in the above-identified patent and that said Letters Patent is hereby corrected as shown below:

Col. 1 at lines 11–13, delete "This research was supported by National Institutes of Health Grants RO1DC03055 and RO1DC3155, so that the United States Government has certain rights herein." and insert --This invention was made with government support under grant numbers RO1DC03055 and RO1DC3155 awarded by the National Institutes of Health. The government has certain rights in this invention.-- in its place.

Signed and Sealed this

Eighth Day of December, 2009

David J. Kappos

David J. Kappos
*Director of the United States Patent and Trademark Office*